(12) United States Patent
Hu et al.

(10) Patent No.: US 8,951,993 B2
(45) Date of Patent: Feb. 10, 2015

(54) PHOSPHORUS CONTAINING COMPOUNDS AS PROTEIN KINASE INHIBITORS

(75) Inventors: Baihua Hu, Audubon, PA (US); Kan He, Montgomery, NJ (US); Minsheng Zhang, Greenbrook, NJ (US)

(73) Assignee: Jiangsu Hansoh Pharmaceutical Co., Ltd. (CN)

(*) Notice: Subject to any disclaimer, the term of this patent is extended or adjusted under 35 U.S.C. 154(b) by 323 days.

(21) Appl. No.: 13/402,335

(22) Filed: Feb. 22, 2012

(65) Prior Publication Data
US 2012/0220551 A1 Aug. 30, 2012

Related U.S. Application Data

(60) Provisional application No. 61/446,321, filed on Feb. 24, 2011.

(51) Int. Cl.
*A61K 31/675* (2006.01)
*A61K 31/685* (2006.01)
*C07F 9/58* (2006.01)
*C07F 9/6509* (2006.01)
*C07F 9/6558* (2006.01)

(52) U.S. Cl.
CPC .................. *C07F 9/582* (2013.01); *C07F 9/588* (2013.01); *C07F 9/650964* (2013.01); *C07F 9/65583* (2013.01)
USPC .............................................. 514/85; 514/89

(58) Field of Classification Search
CPC . C07F 9/588; C07F 9/650964; C07F 9/65583
USPC ...................................................... 514/85, 89
See application file for complete search history.

(56) References Cited

U.S. PATENT DOCUMENTS 7,230,098 B2 6/2007 Cui et al.

FOREIGN PATENT DOCUMENTS

WO WO 2009/143389 A1 11/2009

OTHER PUBLICATIONS

Schiering et al., Crystal Structure of the Tyrosine Kinase Domain of the Hepatocyte Growth Factor Receptor c-Met and its Complex with the Microbial AlkaloidK-252a, PNAS, vol. 100(22), pp. 12654-12659, Oct. 28, 2003, p. 12655-p. 12658.
Choi et al., EML4-ALK Mutations in Lung Cancer that Confer Resistance ALK Inhibitors, N Engl J Med 363, pp. 1734-1739, 2010, Abstract; p. 1736, col. 2, para 3-4; p. 1739, col. 1, para 1.
International Search Report and Written Opinion, International Application No. PCT/US12/26083, Feb. 22, 2012.
Ardini, E., P. Magnaghi, et al. (2010). "Anaplastic Lymphoma Kinase: role in specific tumours, and development of small molecule inhibitors for cancer therapy" Cancer Lett. 299(2): 81-94.
Bilsland, J. G., A. Wheeldon, et al. (2008). "Behavioral and neurochemical alterations in mice deficient in anaplastic lymphoma kinase suggest therapeutic potential for psychiatric indications" Neuropsychopharmacology 33(3): 685-700.
Bossi, R. T., M. B. Saccardo, et al. (2010). "Crystal structures of anaplastic lymphoma kinase in complex with ATP competitive inhibitors." Biochemistry 49(32): 6813-6825. Mctigue, M., Y. Deng, et al. (2010). "Structure of the human anaplastic lymphoma kinase in complex with crizotinib (PF-02341066)" Protein database (2XP2).
Chen, Y., J. Takita, et al. (2008). "Oncogenic mutations of ALK kinase in neuroblastoma" Nature 455(7215): 971-974.
Choi, Y. L., M. Soda, et al. (2010). "EML4-ALK mutations in lung cancer that confer resistance to ALK inhibitors" N. Engl. J. Med. 363(18): 1734-1739.
Chou, Ting-Chao (2006). "Theoretical basis, experimental design, and computerized simulation of synergism and antagonism in drug combination studies" The American Society for Pharmacology and Experimental Therapeutics Pharmacol Rev. 58:621-681.
Christensen, J. G., J. Burrows, et al. (2005). "c-Met as a target for human cancer and characterization of inhibitors for therapeutic intervention" Cancer Lett. 225(1): 1-26.
Danilkovitch-Miagkova, A. and B. Zbar (2002). "Dysregulation of Met receptor tyrosine kinase activity in invasive tumors" J. Clin. Invest. 109(7): 863-867;.
George, R. E., T. Sanda, et al. (2008). "Activating mutations in ALK provide a therapeutic target in neuroblastoma" Nature 455(7215): 975-978.
Hallberg, B. and R. H. Palmer (2010). "Crizotinib—latest champion in the cancer wars?" N. Engl. J. Med. 363(18): 1760-1762.
Iwahara, T., J. Fujimoto, et al. (1997). "Molecular characterization of ALK, a receptor tyrosine kinase expressed specifically in the nervous system" Oncogene 14(4): 439-449.
Janoueix-Lerosey, Lequin et al. 2008. "Somatic and germline activating mutations of the ALK kinase receptor in neuroblastoma" Nature 455(7215): 967-970.
Knight, Z. A., H. Lin, et al. (2010). "Targeting the cancer kinome through polypharmacology" Nat. Rev. Cancer 10(2): 130-137.

(Continued)

*Primary Examiner* — San-Ming Hui
(74) *Attorney, Agent, or Firm* — Brinks Gilson & Lione

(57) ABSTRACT

The present invention relates to compounds represented by formula (I), which can modulate the activity of protein kinases. The invention also relates to a composition containing a compound of formula (I), and a method for synthesizing and using such compound for preventing or treating ALK or cMet mediated disorders or conditions.

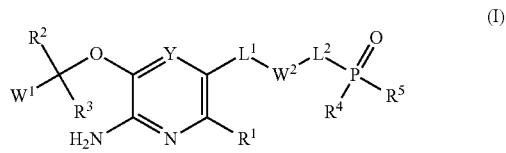

(I)

33 Claims, No Drawings

(56) References Cited

OTHER PUBLICATIONS

Kwak, Bang et al. 2010. "Anaplastic lymphoma kinase inhibition in non-small-cell lung cancer" N. Engl. J. Med. 363(18): 1693-1703.

Lee, C. C., Y. Jia, et al. (2010). "Crystal structure of the ALK (anaplastic lymphoma kinase) catalytic domain" Biochem. J. 430(3): 425-437.

Manning, G., D. B. Whyte, et al. (2002), "The protein kinase complement of the human genome" Science 298(5600): 1912-1934.

Ott, Gregory R. (2011). "2,7-Disubstituted-pyrrolo[2,1-f][1,2,4] triazines: New variant of an old template and application to the discovery of anaplastic lymphoma kinase (ALK) inhibitors with in vivo antitumor activity" Journal of Medicinal Chemistry 54, 6328-6341.

Milkiewicz, K. L. and G. R. Ott (2010). "Inhibitors of anaplastic lymphoma kinase: a patent review." Expert Opin. Ther. Pat. 20(12): 1653-1681.

Morris, S. W., M. N. Kirstein, et al. (1994). "Fusion of a kinase gene, ALK, to a nucleolar protein gene, NPM, in non-Hodgkin's lymphoma" Science 263(5151): 1281-1284.

Morris, S. W., C. Naeve, et al. (1997). "ALK, the chromosome 2 gene locus altered by the t(2;5) in non-Hodgkin's lymphoma, encodes a novel neural receptor tyrosine kinase that is highly related to leukocyte tyrosine kinase (LTK)" Oncogene 14(18): 2175-2188.

Mosse, Y. P., M. Laudenslager, et al. (2008). "Identification of ALK as a major familial neuroblastoma predisposition gene" Nature 455(7215): 930-935.

Palmer, R. H., E. Vernersson, et al. (2009). "Anaplastic lymphoma kinase: signalling in development and disease" Biochem. J. 420(3): 345-361.

Passoni, L., L. Longo, et al. (2009). "Mutation-independent anaplastic lymphoma kinase overexpression in poor prognosis neuroblastoma patients." Cancer Res. 69(18): 7338-7346.

Pulford, K., L. Lamant, et al. (1997). "Detection of anaplastic lymphoma kinase (ALK) and nucleolar protein nucleophosmin (NPM)-ALK proteins in normal and neoplastic cells with the monoclonal antibody ALK1" Blood 89(4): 1394-1404).

Rikova, K., A. Guo, et al. (2007). "Global survey of phosphotyrosine signaling identifies oncogenic kinases in lung cancer" Cell 131(6): 1190-1203.

Shiota, M., J. Fujimoto, et al. (1994). "Hyperphosphorylation of a novel 80 kDa protein-tyrosine kinase similar to Ltk in a human Ki-1 lymphoma cell line, AMS3" Oncogene 9(6): 1567-1574.

Soda, M., Y. L. Choi, et al. (2007). "Identification of the transforming EML4-ALK fusion gene in non-small-cell lung cancer" Nature 448(7153): 561-566.

Soda, M., S. Takada, et al. (2008). "A mouse model for EML4-ALK-positive lung cancer" Proc. Natl. Acad. Sci. U. S. A. 105(50): 19893-19897.

Stoica, G. E., A. Kuo, et al. (2001). "Identification of anaplastic lymphoma kinase as a receptor for the growth factor pleiotrophin" J. Biol. Chem. 276(20): 16772-16779.

Stoica, G. E., A. Kuo, et al. (2002). "Midkine binds to anaplastic lymphoma kinase (ALK) and acts as a growth factor for different cell types" J. Biol. Chem. 277(39): 35990-35998.

Webb, T. R., J. Slavish, et al. (2009). "Anaplastic lymphoma kinase: role in cancer pathogenesis and small-molecule inhibitor development for therapy" Expert Rev. Anticancer Ther. 9(3): 331-356.

Yanagisawa, H., Y. Komuta, et al. (2010). "Pleiotrophin induces neurite outgrowth and up-regulates growth-associated protein (GAP)-43 mRNA through the ALK/GSK3beta/beta-catenin signaling in developing mouse neurons" Neurosci. Res. 66(1): 111-116.

PHOSPHORUS CONTAINING COMPOUNDS AS PROTEIN KINASE INHIBITORS

CROSS-REFERENCE TO RELATED APPLICATION AND INCORPORATION BY REFERENCE

The present application claims priority to U.S. Provisional Patent Application No. 61/446,321, filed Feb. 24, 2011, the entirety of which is hereby incorporated by reference.

TECHNICAL FIELD

This invention is directed to compounds that modulate protein kinase activities and therefore are useful in the prevention and treatment of protein kinase related disorders. More particularly, this invention provides phosphorus containing compounds that modulate activities of anaplastic lymphoma kinase (ALK) and cMet kinase, methods of synthesizing, and using such compounds for preventing or treating ALK or cMet mediated disorders or conditions.

BACKGROUND

Kinases are a superfamily of enzymes that transfer a phosphate group from ATP to target proteins. There are more than 518 kinases encoded in the human genome, including 90 tyrosine kinases, 388 serine/threnine kinases and 40 atypical kinases (Manning, G., D. B. Whyte, et al. (2002), "The protein kinase complement of the human genome" Science 298 (5600): 1912-1934). They play vital roles in cell activation, proliferation, differentiation, migration, vascular permeability, etc. Dysfunction of kinases has been implicated in various diseases such as cancer, inflammation, cardiovascular diseases, diabetes, and neuronal disorders. Several kinase inhibitors have been developed for the treatment of cancers, including but not limited to imatinib, dasatinib, nilotinib, gefitinib, erlotinib, lapatinib, sunitinib, sorafenib, pazopanib, evrolimus, trastuzumab, cetuximab, panitumumab, bevacizumab (Knight, Z. A., H. Lin, et al. (2010). "Targeting the cancer kinome through polypharmacology" Nat. Rev. Cancer 10(2): 130-137).

Anaplastic lymphoma kinase (ALK) is a receptor tyrosine kinase in the insulin receptor family. Other members of the family include lymphocyte tyrosine kinase, insulin receptor kinase, IGF-1 receptor kinase, RTK neutrophin receptor kinases and hepatocyte growth factor/scatter factor (Met) kinase. ALK, which was initially discovered by cloning of the nucleolar protein nucleophosmin (NPM)-ALK fusion gene in anaplastic large cell lymphomas, is encoded by a genomic locus at the chromosomal band 2p23 in the human (Morris, S. W., M. N. Kirstein, et al. (1994). "Fusion of a kinase gene, ALK, to a nucleolar protein gene, NPM, in non-Hodgkin's lymphoma" Science 263(5151): 1281-1284; Shiota, M., J. Fujimoto, et al. (1994). "Hyperphosphorylation of a novel 80 kDa protein-tyrosine kinase similar to Ltk in a human Ki-1 lymphoma cell line, AMS3" Oncogene 9(6): 1567-1574). The genes encoding native, full length receptor forms of ALK in human and mouse were cloned in 1997 (Iwahara, T., J. Fujimoto, et al. (1997). "Molecular characterization of ALK, a receptor tyrosine kinase expressed specifically in the nervous system" Oncogene 14(4): 439-449; Morris, S. W., C. Naeve, et al. (1997). "ALK, the chromosome 2 gene locus altered by the t(2; 5) in non-Hodgkin's lymphoma, encodes a novel neural receptor tyrosine kinase that is highly related to leukocyte tyrosine kinase (LTK)" Oncogene 14(18): 2175-2188). The single chain of native ALK protein consists of 1620 amino acids with posttranslational modifications, forming LDL-A, MAM, glycine-rich, transmembrane, and catalytic domains. There are three tyrosine residues (Tyr1278, Tyr1282 and Tyr1283) forming the autophosphorylation motif YxxxYY in the activation loop, a common structural feature found with insulin and IGF1 receptor kinases. The sequential phosphorylation of this tyrosine triplet regulates kinase activity. Recently, X-ray crystal structures of the ALK catalytic domain were determined in apo, ADP-, or inhibitor-bound forms (Bossi, R. T., M. B. Saccardo, et al. (2010). "Crystal structures of anaplastic lymphoma kinase in complex with ATP competitive inhibitors." Biochemistry 49(32): 6813-6825; Lee, C. C., Y. Jia, et al. (2010). "Crystal structure of the ALK (anaplastic lymphoma kinase) catalytic domain" Biochem J 430(3): 425-437; Mctigue, M., Y. Deng, et al. (2010). "Structure of the human anaplastic lymphoma kinase in complex with crizotinib (PF-02341066)" Protein database (2XP2)). ALK shares the basic tyrosine kinase domain architecture and topology. A small N-terminal lobe is connected to a larger C-terminal lobe by a loop referred to as the hinge region, in which E1197 and M1199 forms important hydrogen bonds with ATP/ADP and inhibitors. The activation loop, which consists of residues 1270-1299, begins with the DFG-motif and ends with residues PPE. The catalytic loop, which consist of residues 1247-1254, positions between alphaE and the first strand of the 2-stranded beta-sheet. The structures reveal important interactions between active site residues and inhibitors, and how the functional mutants affect the kinase activity.

The native ALK is dominantly expressed in the central and peripheral nervous systems during development (Iwahara, T., J. Fujimoto, et al. (1997). "Molecular characterization of ALK, a receptor tyrosine kinase expressed specifically in the nervous system" Oncogene 14(4): 439-449; Morris, S. W., C. Naeve, et al. (1997). "ALK, the chromosome 2 gene locus altered by the t(2; 5) in non-Hodgkin's lymphoma, encodes a novel neural receptor tyrosine kinase that is highly related to leukocyte tyrosine kinase (LTK)" Oncogene 14(18): 2175-2188). As reported by Iwahara et al., the ALK mRNA was detected in thalamus, hypothalamus, mid brain, dorsal root ganglia and olfactory bulb in mouse from day 11. However, the expression level decreased near the gestation, and become barely detectable in adult mouse. ALK expression was only observed in rare scattered neural cells, endothelial cell and pericytes in nervous system in adult and human tissues (Iwahara, T., J. Fujimoto, et al. (1997). "Molecular characterization of ALK, a receptor tyrosine kinase expressed specifically in the nervous system" Oncogene 14(4): 439-449; Pulford, K., L. Lamant, et al. (1997). "Detection of anaplastic lymphoma kinase (ALK) and nucleolar protein nucleophosmin (NPM)-ALK proteins in normal and neoplastic cells with the monoclonal antibody ALK1" Blood 89(4): 1394-1404). The restricted tissue expression pattern suggests that ALK plays an important role in the development and function of nervous system. Consistently, ALK receptor was demonstrated as the receptor for growth factors pleiotrophin and midkine for neurite outgrowth (Stoica, G. E., A. Kuo, et al. (2001). "Identification of anaplastic lymphoma kinase as a receptor for the growth factor pleiotrophin" J. Biol. Chem. 276(20): 16772-16779; Stoica, G. E., A. Kuo, et al. (2002). "Midkine binds to anaplastic lymphoma kinase (ALK) and acts as a growth factor for different cell types" J. Biol. Chem. 277(39): 35990-35998; Yanagisawa, H., Y. Komuta, et al. (2010). "Pleiotrophin induces neurite outgrowth and up-regulates growth-associated protein (GAP)-43 mRNA through the ALK/GSK3beta/beta-catenin signaling in developing mouse neurons" Neurosci. Res. 66(1): 111-116). Furthermore, the ALK knockout mice displayed an increased struggling time in the tail suspension test and the Porsolt swim test and enhanced performance in a novel object-recognition test (Bilsland, J. G., A. Wheeldon, et al. (2008). "Behavioral and neurochemical alterations in mice deficient in anaplastic lymphoma kinase suggest therapeutic potential for psychiatric indications" Neuropsychopharmacology 33(3): 685-700). An age-dependent increase in basal hippocampal progenitor proliferation was observed, similar to what is observed after chronic treatment with antidepressants. Other than that, the animals developed normally with no anatomical abnormalities and a full life span. Collectively, these results suggest that ALK could be a new therapeutic target for psychiatric indications, such as schizophrenia and depression.

Overexpression, mutation and fusion proteins of ALK have been implicated in several cancers, including but not limited to neuroblastoma, anaplastic large-cell lymphoma (ALCL), non-small cell lung cancer (NSCLC) and inflammatory myofibroblastic tumor (IMT). When its kinase activity is constitutively enhanced by point mutation, amplification or rearrangement of the corresponding genes, ALK become an oncogenic driver, activating numerous signaling pathways to promote tumorigenesis (Palmer, R. H., E. Vernersson, et al. (2009). "Anaplastic lymphoma kinase: signalling in development and disease" Biochem. J. 420(3): 345-361). The signal pathways include those involving Ras and mitogen-activated protein kinase (MAPK), phosphatidylinositol 3-kinase (PI3K), protein kinase B (Akt), and target of rapamycin (TOR), sonic hedgehog (Shh), phospholipase Cγ (PLCγ), JUN kinase, Janus kinase (JAK) and signal transducer and activator of transcription (STAT).

Neuroblastoma is an embryonal tumor of the peripheral sympathetic nervous system, accounting for approximately 15% of all deaths due to childhood cancer. Overexpression and point mutations of full-length ALK plays an important role in the pathogenesis of neuroblastoma (Chen, Y., J. Takita, et al. (2008). "Oncogenic mutations of ALK kinase in neuroblastoma" Nature 455(7215): 971-974; George, R. E., T. Sanda, et al. (2008). "Activating mutations in ALK provide a therapeutic target in neuroblastoma" Nature 455(7215): 975-978; Janoueix-Lerosey, Lequin et al. 2008. "Somatic and germline activating mutations of the ALK kinase receptor in neuroblastoma" Nature 455(7215): 967-970; Mosse, Y. P., M. Laudenslager, et al. (2008). "Identification of ALK as a major familial neuroblastoma predisposition gene" Nature 455(7215): 930-935; Passoni, L., L. Longo, et al. (2009). "Mutation-independent anaplastic lymphoma kinase overexpression in poor prognosis neuroblastoma patients." Cancer Res. 69(18): 7338-7346). There are copy number increases of ALK in more than 25% and mis-sense mutations in 6-8% of the primary neuroblastomas. The mutants identified include but not limited to F1174L, R1257Q, G1128A, M1166R, I1171N, F1174I, R1192P, F1245C, F1245V, I1250T, I1250V, T10871, K1062M and Y1278S. Among of them, F1174L is the most frequent somatic mutant, identified in approximately 4% of primary tumors. R1257Q is the mutant identified in both familial and sporadic tumors. Most of the mutations map to critical regions of the kinase domain and are oncogenic drivers. Mutated ALK proteins are over-expressed, hyper-phosphorylated and show constitutive kinase activity in primary neuroblastomas. The knockdown of ALK expression or inhibition of ALK activity by small molecule inhibitors in ALK-mutated cells, and in cell lines over-expressing a wild-type ALK, led to a marked decrease of cell proliferation. Altogether, the available data identify ALK as a critical player in neuroblastoma development, and may represent a very attractive therapeutic target for the treatment of this disease that is still frequently fatal with current treatments.

ALCL is a rare form of indolent Non-Hodgkin's lymphoma that affects T-cells. It is more common in children and men. ALCL often affects the lymph nodes, skin, liver, lungs, and bone marrow. This disease can be either systematic or cutaneous. Approximately 60-80% ACLC is ALK positive (Morris, S. W., M. N. Kirstein, et al. (1994). "Fusion of a kinase gene, ALK, to a nucleolar protein gene, NPM, in non-Hodgkin's lymphoma" Science 263(5151): 1281-1284). The most frequent ALK fusion protein is NPM-ALK, being found in 75-80% of all ALK-positive ALCL patients. Other ALK fusion proteins include but not limited to TPM3-, ATIC-, CLTC-, TFGL-, TFG-, TMP4-ALK. The CLTC-, NPM- or TMP3-ALK (Webb, T. R., J. Slavish, et al. (2009). "Anaplastic lymphoma kinase: role in cancer pathogenesis and small-molecule inhibitor development for therapy" Expert Rev Anticancer Ther. 9(3): 331-356). ALK-fusion proteins are also found in rare cases of diffuse large B-cell lymphoma and systemic histiocytosis. ALK fusion proteins mediate oncogenesis by activating the classical receptor tyrosine kinase pathway, and most relevantly, the STAT3 phosphorylation and activation. Transgenic mouse expressing NPM-ALK develop large cell lymphoma with a T-cell phenotype and frequent expression of CD30 antigen. ALK has been shown to be a valid therapeutic target for ALCL.

Lung cancer is the leading cause of cancer mortality in the world today. Approximately 85% of the lung cancer is non-small cell lung cancer (NSCLC). ALK gene rearrangement was identified in a small subset (6-7%) of NSCLC patients, involving a small inversion within chromosome 2p to form a fusion gene comprising portions of the echinoderm microtubule-associated protein-like 4 (EML4) gene and the ALK gene (Rikova, K., A. Guo, et al. (2007). "Global survey of phosphotyrosine signaling identifies oncogenic kinases in lung cancer" Cell 131(6): 1190-1203; Soda, M., Y. L. Choi, et al. (2007). "Identification of the transforming EML4-ALK fusion gene in non-small-cell lung cancer" Nature 448(7153): 561-566). In lung cancer, ALK fusion proteins appear to be restricted to patients with adenocarcinoma, mostly in patients with minimal or no smoking history. ALK abnormalities seem to be mutually exclusive to EGFR and KRAS mutations. Other fusion proteins in NSCLC include but not limited to TGF-ALK, KIF5B-ALK. Auto-phosphorylation of EML4-ALK activates PI3K-AKT and RAS-MAPK pathways, leading to cell growth, proliferation, survival, and cell cycle progression. The oncogenic potential of EML4-ALK was confirmed in transgenic mice that developed hundreds of adenocarcinoma nodules in both lung, and the tumor burden was effectively reduced by administration of an potent ALK inhibitor (Soda, M., S. Takada, et al. (2008). "A mouse model for EML4-ALK-positive lung cancer" Proc. Natl. Acad. Sci. U.S.A. 105(50): 19893-19897). Furthermore, the inhibition of ALK in lung cancer by oral administration of crizotinib, an ALK/cMet inhibitor, resulted in tumor shrinkage or stable disease in most patients. Altogether, ALK is an attractive therapeutic target for NSCLC (Kwak, Bang et al. 2010. "Anaplastic lymphoma kinase inhibition in non-small-cell lung cancer" N. Engl. J. Med. 363(18): 1693-1703).

IMT are uncommon lesions composed of spindled myofibroblasts within a variable background of collagen and inflammatory cells. The frequency of ALK expression in IMT ranges from 36-62%. Several ALK fusion proteins were identified in IMT patients, such as TPM3-, TPM4-, CLTC-, ATIC-, CARS-, RANBP2- and SEC31L1-ALK (Webb, T. R., J. Slavish, et al. (2009). "Anaplastic lymphoma kinase: role in cancer pathogenesis and small-molecule inhibitor development for therapy" Expert Rev. Anticancer Ther. 9(3): 331-356). Other tumors with ALK gene rearrangement include, but not limited to, B-cell Non-Hodgkin Lymphoma, oesophageal squamous cell carcinoma and systemic histiocytosis (Webb, T. R., J. Slavish, et al. (2009). "Anaplastic lymphoma kinase: role in cancer pathogenesis and small-molecule inhibitor development for therapy" Expert Rev. Anticancer Ther. 9(3): 331-356). With more specific and sensitive assays for ALK detection, it is expected that ALK may play a role in more tumors than those identified so far.

Several small molecule inhibitors of ALK have been reported elsewhere, for example, crizotinib (PF-02341066) is currently under clinical development for lung cancer, ALCL and IMT (Ardini, E., P. Magnaghi, et al. (2010). "Anaplastic Lymphoma Kinase: role in specific tumours, and development of small molecule inhibitors for cancer therapy" Cancer Lett. 299(2): 81-94; Milkiewicz, K. L. and G. R. Ott (2010). "Inhibitors of anaplastic lymphoma kinase: a patent review." Expert Opin. Ther. Pat. 20(12): 1653-1681). Crizotinib inhibits ALK and cMet activities and proliferation of several ALK positive cancer cell lines. Crizotinib is effective in xenograft cancer models. It is noteworthy that Crizotinib was reported to be a time-dependent cytochrome P450 3A4 inhibitor, causing clinical drug-drug interactions. In the reported phase I study, crizotinib was effective against advanced non-small cell lung cancers carrying activated ALK. The overall response rate was 57% and the rate of stable disease was 33%. The response rate is impressive, as compared with the approximately 10% response rate in such cancers that were treated with second-line chemotherapy. However, two secondary drug-resistance mutations in the catalytic domain, L1196M and C1156Y, were observed in a patient who has an initial strong clinical response to crizotinib (Choi, Y. L., M. Soda, et al. (2010). "EML4-ALK mutations in lung cancer that confer resistance to ALK inhibitors" N. Engl. J. Med. 363(18): 1734-1739). Each mutation developed independently in sub-clones of the tumor and conferred marked resistance to two different ALK inhibitors. The appearance of crizotinib-resistance mutations indicates that additional ALK inhibitors will be required to target EML4-ALK mutants that are insensitive to crizotinib in a clinical settings (Hallberg, B. and R. H. Palmer (2010). "Crizotinib—latest champion in the cancer wars?" N. Engl. J. Med. 363(18): 1760-1762).

cMet is a high-affinity hepatocyte growth factor receptor (HGF). cMet/HGF/SF signaling is essential for normal cell proliferation, migration, angiogenesis, embryogenesis, organogenesis, and tissue regeneration (Danilkovitch-Miagkova, A. and B. Zbar (2002). "Dysregulation of Met receptor tyrosine kinase activity in invasive tumors" J. Clin. Invest. 109(7): 863-867; Christensen, J. G., J. Burrows, et al. (2005). "c-Met as a target for human cancer and characterization of inhibitors for therapeutic intervention" Cancer Lett. 225(1): 1-26). Aberrant cMet/HGF/SF signaling, resulting from mutation or over-expression of the c-Met proto-oncogene and HGF, plays a major role in tumorigenesis, invasion, and metastasis many human tumors. cMet is highly expressed in numerous cancers, and the expression correlates with poor patient prognosis. cMet activating point mutations in the kinase domain are implicated as the cause of hereditary papillary renal carcinoma and were also detected in sporadic papillary renal carcinoma, lung cancers, head and neck cancers, childhood hepatocellular carcinoma, and gastric cancer. Furthermore, amplification of the cMet gene locus was detected in patients with gastric, metastatic colorectal cancer, and esophageal adenocarcinoma. cMet is an attractive therapeutic target for cancer treatment (Christensen, J. G., J. Burrows, et al. (2005). "c-Met as a target for human cancer and characterization of inhibitors for therapeutic intervention" Cancer Lett. 225(1): 1-26).

Accordingly, the identification of small-molecules that specifically modulate kinase activity, particularly ALK and/or cMet kinase, serves therapeutic approaches for treatment of cancers, inflammation, cardiovascular and metabolic diseases, psychological and neurological disorders.

SUMMARY

In one aspect, the compounds are of the formula (I):

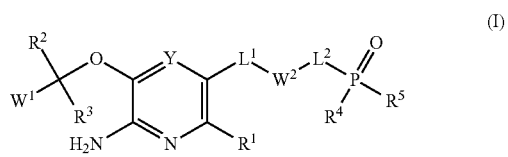

where $W^1$, $W^2$, $L^1$, $L^2$, Y, $R^1$, $R^2$, $R^3$, $R^4$ and $R^5$ are as defined below. Salts, solvates, hydrates, and metabolites of these compounds are also within the scope of the invention.

In another aspect, the compounds are of the formula (Ia):

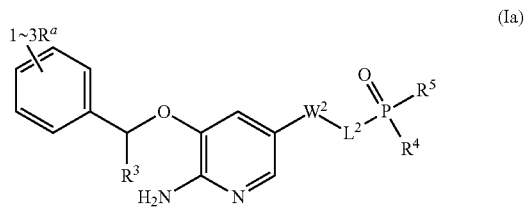

where $W^2$, $L^2$, $R^a$, $R^3$, $R^4$ and $R^5$ are as defined below. Salts, solvates, hydrates, and metabolites of these compounds are also within the scope of the invention.

In yet another aspect, the compounds are of the formula (Ic):

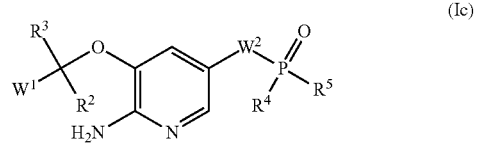

wherein $W^1$ is $C_{6-12}$ aryl substituted with three substituents; $W^2$ is selected from the group consisting of unsubstituted or substituted $C_{6-12}$ aryl, and unsubstituted or substituted 3- to 12-membered heteroaryl;
$R^1$ is hydrogen;
$R^2$ and $R^3$ are independently selected from the group consisting of hydrogen, and unsubstituted or substituted alkyl; and
$R^4$ and $R^5$ are independently selected from the group consisting —$OR^6$, and unsubstituted or substituted alkyl, wherein $R^6$ is selected from the group consisting of hydrogen, halogen, and unsubstituted or substituted $C_{1-12}$ alkyl.

In still another aspect, the present disclosure provides methods for the prevention and treatment of diseases associated with ALK or cMet activities.

In still another aspect, the present disclosure provides methods for preparing the compound of formula (I).

In addition to the compounds provided herein, the present disclosure provides a composition containing one or more of these compounds.

DETAILED DESCRIPTION OF THE INVENTION

This invention relates generally to compounds that modulate protein tyrosine kinase activity, methods of synthesizing, and using such compounds in therapeutic methods.

When describing the compounds, compositions, methods and processes of this disclosure, the following terms have the following meanings, unless otherwise indicated.

The term "halogen" or "halo" means a chlorine, bromine, iodine, or fluorine atom.

The term "alkyl" means a hydrocarbon group that may be linear, cyclic, or branched or a combination thereof having the number of carbon atoms designated (i.e., $C_{2-12}$ means two to twelve carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl groups include haloalkyl, thioalkyl, aminoalkyl, and the like.

The term "alkenyl" means a hydrocarbon group that contains at least one carbon-to-carbon double bond. Alkenyl groups can include, e.g., allyl, 1-butenyl, 2-hexenyl and 3-octenyl groups. The term "alkynyl" means a hydrocarbon group that contains at least one carbon-to-carbon triple bond. Alkynyl groups can include, e.g., ethynyl, propargyl, and 3-hexynyl. Alkenyl and alkynyl groups can be substituted or unsubstituted, unless otherwise indicated.

The term "aryl" means a polyunsaturated, aromatic hydrocarbon group having 5-10 atoms and forming a single ring (monocyclic, preferably with 6 atoms such as phenyl) or multiple rings (bicyclic (preferably with 10 atoms such as naphthyl) or polycyclic), which can be fused together or linked covalently. Examples of aryl groups include phenyl and naphthalene-1-yl, naphthalene-2-yl, biphenyl and the like. Aryl groups can be substituted or unsubstituted, unless otherwise indicated.

The term "heteroaryl" means an aromatic group containing 5-10 atoms and at least one heteroatom (such as S, N, O, Si), where the heteroaryl group may be monocyclic (with preferably 5 or 6 atoms) or bicyclic (with preferably 9 or 10 atoms). Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

The term "cycloalkyl" refers to saturated monocyclic, bicyclic, tricyclic, or other polycyclic hydrocarbon groups. Any atom can be substituted, e.g., by one or more substituents. A ring carbon serves as the point of attachment of a cycloalkyl group to another moiety. Cycloalkyl groups can contain fused rings. Fused rings are rings that share a common carbon atom. Cycloalkyl moieties can include, e.g., cyclopropyl, cyclobutyl, cyclopentyl, cyclohexyl, cycloheptyl, adamantyl, and norbornyl(bicycle[2.2.1]heptyl).

The term "aralkyl" refers to an alkyl moiety in which an alkyl hydrogen atom is replaced by an aryl group. One of the carbons of the alkyl moiety serves as the point of attachment of the aralkyl group to another moiety. Aralkyl includes groups in which more than one hydrogen atom on an alkyl moiety has been replaced by an aryl group. Any ring or chain atom can be substituted e.g., by one or more substituents. Non-limiting examples of "aralkyl" include benzyl, 2-phenylethyl, 3-phenylpropyl, benzhydryl (diphenylmethyl), and trityl (triphenylmethyl) groups.

The term "heteroaralkyl" refers to an alkyl moiety in which an alkyl hydrogen atom is replaced by a heteroaryl group. One of the carbons of the alkyl moiety serves as the point of attachment of the aralkyl group to another moiety. Heteroaralkyl includes groups in which more than one hydrogen atom on an alkyl moiety has been replaced by a heteroaryl group. Any ring or chain atom can be substituted e.g., by one or more substituents. Heteroaralkyl can include, for example, 2-pyridylethyl.

The term "heterocyclyl" or "heterocyclic", which are synonymous as used herein, means a saturated or unsaturated non-aromatic ring containing at least 5-10 atoms (preferably 5 or 6) and at least one heteroatom (typically 1 to 5 heteroatoms) selected from nitrogen, oxygen or sulfur. The heterocyclyl ring may be monocyclic (with preferably 5 or 6 atoms) or bicyclic (with preferably 9 or 10 atoms). The ring system has 1-4 heteroatoms if monocyclic, 1-8 heteroatoms if bicyclic, or 1-10 heteroatoms if tricyclic, the heteroatoms selected from O, N, or S (and mono and dioxides thereof, e.g., N→O⁻, S(O), SO₂). The heterocyclyl groups can contain fused rings. Fused rings are rings that share a common carbon atom. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

The term "ring" means a compound whose atoms are arranged in formulas in a cyclic form. The ring compound can be either carbocyclic or heterocyclic.

The term "alkoxy" refers to an —O-alkyl radical. The term "mercapto" refers to an SH radical. The term "thioalkoxy" refers to an —S-alkyl radical. The terms "aryloxy" and "heteroaryloxy" refer to an —O-aryl radical and —O-heteroaryl radical, respectively. The terms "thioaryloxy" and "thioheteroaryloxy" refer to an —S-aryl radical and —S-heteroaryl radical, respectively.

The terms "aralkoxy" and "heteroaralkoxy" refer to an —O-aralkyl radical and —O-heteroaralkyl radical, respectively. The terms "thioaralkoxy" and "thioheteroaralkoxy" refer to an —S-aralkyl radical and —S-heteroaralkyl radical, respectively. The term "cycloalkoxy" refers to an —O-cycloalkyl radical. The terms "cycloalkenyloxy" and "heterocycloalkenyloxy" refer to an —O-cycloalkenyl radical and —O-heterocycloalkenyl radical, respectively. The term "heterocyclyloxy" refers to an —O-heterocyclyl radical. The term "thiocycloalkoxy" refers to an —S-cycloalkyl radical. The terms "thiocycloalkenyloxy" and "thioheterocycloalkenyloxy" refer to an —S-cycloalkenyl radical and —S-heterocycloalkenyl radical, respectively. The term "thioheterocyclyloxy" refers to an —S-heterocyclyl radical.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be substituted e.g., by one or more substituents. The cycloalkenyl groups can contain fused rings. Fused rings are rings that share a common carbon atom. Cycloalkenyl moieties can include, e.g., cyclohexenyl, cyclohexadienyl, or norbornenyl.

The term "heterocycloalkenyl" refers to partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (and mono and dioxides thereof, e.g., N→O$^-$, S(O), SO$_2$) (e.g., carbon atoms and 1-4, 1-8, or 1-10 heteroatoms of N, O, or S if monocyclic, bicyclic, or tricyclic, respectively). A ring carbon (e.g., saturated or unsaturated) or heteroatom is the point of attachment of the heterocycloalkenyl substituent. Any atom can be substituted, e.g., by one or more substituents. The heterocycloalkenyl groups can contain fused rings. Fused rings are rings that share a common carbon atom. Heterocycloalkenyl groups can include, e.g., tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, heteroaryl, arylcycloalkyl, heteroarylcycloalkyl, arylcycloalkenyl, heteroarylcycloalkenyl, arylheterocyclyl, heteroarylheterocyclyl, arylheterocycloalkenyl, or heteroaryl-heterocycloalkenyl group at any atom of that group. In one aspect, the substituent(s) (e.g., $R^a$) on a group are independently any one single, or any combination of two or more of the permissible atoms or groups of atoms delineated for that substituent. In another aspect, a substituent may itself be substituted with any one of the above substituents (e.g., $R^b$).

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

All of the above terms (e.g., "alkyl," "aryl," "heteroaryl" etc.), in some embodiments, include both substituted and unsubstituted forms of the indicated groups. These groups may be substituted multiple times, as chemically allowed.

The term "composition" as used herein is intended to encompass a product comprising the specified ingredients in the specified amounts, as well as any product which results, directly or indirectly, from combination of the specified ingredients in the specified amounts. By "pharmaceutically-acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoe thanol, 2-dimethylaminoe thanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", J. Pharmaceutical Science, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient. Salts are especially the pharmaceutically acceptable salts of compounds of formula (I).

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The term "metabolite" refers to the intermediate and product of metabolism.

"Therapeutically effective amount" refers to an amount sufficient to effect treatment when administered to a patient in need of treatment.

"Treating" or "treatment" as used herein refers to the treating or treatment of a disease or medical condition (such as a cancer) in a patient, such as a mammal (particularly a human or a companion animal) which includes:

ameliorating the disease or medical condition, i.e., eliminating or causing regression of the disease or medical condition in a patient;

suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention.

Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

A compound of formula (I) can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound according to the invention is not only for management of humans, but also for the treatment of other warm-blooded animals, for example of commercially useful animals. Such a compound may also be used as a reference standard in the test systems described above to permit a comparison with other compounds.

In one aspect, the invention provides a compound of formula (I):

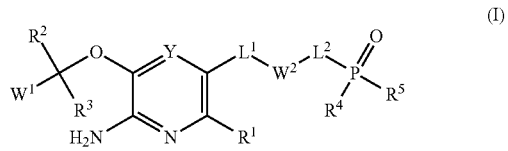

wherein Y is N, or CR$^6$;

L$^1$ and L$^2$ are independently selected from the group consisting of a bond, —O—, —N(H)—, —S—, —OR$^6$—, —SR$^6$—, —NR$^6$—, —R$^6$NR$^7$—, —R$^6$OR$^7$—, —C(O)N(R$^6$)—, —NR$^6$C(O)—, —C(O)NR$^6$—, —R$^6$S(O)$_2$—, —R$^6$S(O)$_r$R$^7$—, S(O)$_2$NR$^7$—, —NR$^6$S(O)$_2$R$^7$—, —C(O)R$^6$—, —OC(O)NR$^6$—, —NR$^6$C(O)NR$^7$—, unsubstituted or substituted alkyl, unsubstituted or substituted alkoxy, unsubstituted or substituted alkthioxy, unsubstituted or substituted aralkoxy, unsubstituted or substituted alkenyl, unsubstituted or substituted alkynyl, unsubstituted or substituted C$_{6-12}$ aryl, unsubstituted or substituted C$_{3-12}$ carbocyclic, unsubstituted or substituted 3- to 12-membered heterocyclyl, and unsubstituted or substituted 3- to 12-membered heteroaryl; where L$^1$ and L$^2$ can be attached to in any position of the group; and where r is an integer from 0-2;

W$^1$ is selected from the group consisting of unsubstituted or substituted C$_{3-12}$ carbocyclic, unsubstituted or substituted C$_{6-12}$ aryl, unsubstituted or substituted 3- to 12-membered heterocyclyl, and unsubstituted or substituted heteroaryl; when C$_{6-12}$ aryl or heteroaryl is substituted with only two substituents, the two substituents are not in para positions;

W$^2$ is selected from the group consisting of unsubstituted or substituted C$_{6-12}$ aryl, and unsubstituted or substituted 3- to 12-membered heteroaryl;

R$^1$ is selected from the group consisting of hydrogen, halogen, unsubstituted or substituted alkyl, unsubstituted or substituted alkenyl, unsubstituted or substituted alkynyl, —SR$^6$, —S(O)R$^6$, —S(O)$_2$R$^6$, —S(O)$_2$NR$^6$R$^7$, —NO$_2$, —NR$^6$R$^7$, —CN, —C(O)R$^6$, —OC(O)R$^6$, —OR$^6$, —C(O)NR$^6$R$^7$, —NR$^6$C(O)R$^7$, unsubstituted or substituted C$_{3-12}$ cycloalkyl, unsubstituted or substituted C$_{6-12}$ aryl, unsubstituted or substituted 3- to 12-membered heterocyclic, and unsubstituted or substituted 5- to 12-membered heteroaryl;

R$^2$ and R$^3$ are independently selected from the group consisting of hydrogen, halogen, unsubstituted or substituted alkyl, unsubstituted or substituted carbocyclic, unsubstituted or substituted C$_{6-12}$ aryl, unsubstituted or substituted 3-12 membered heterocyclic, and unsubstituted or substituted 5-12 membered heteroaryl; or R$^2$ and R$^3$ may combine with an atom or atoms to which they are attached to form unsubstituted or substituted C$_{3-12}$ cycloalkyl, unsubstituted or substituted 3- to 12-membered heterocyclic, unsubstituted or substituted C$_{6-12}$ aryl, or unsubstituted or substituted 5- to 12-membered heteroaryl; and R$^4$ and R$^5$ are independently selected from the group consisting —OR$^6$, —NR$^6$, unsubstituted or substituted alkyl, unsubstituted or substituted alkenyl, unsubstituted or substituted alkynyl, and unsubstituted or substituted C$_3$-C$_{10}$ cycloalkyl; or R$^4$ and R$^5$ together with atom(s) to which they are attached form an unsubstituted or substituted 3- to 12-membered ring;

wherein R$^6$ and R$^7$ are independently selected from the group consisting of hydrogen, halogen, unsubstituted or substituted $C_{1-12}$ alkyl, unsubstituted or substituted $C_{2-12}$ alkenyl, unsubstituted or substituted $C_{2-12}$ alkynyl, unsubstituted or substituted $C_{3-12}$ cycloalkyl, unsubstituted or substituted $C_{6-12}$ aryl, unsubstituted or substituted 3-12 membered heterocyclic, and unsubstituted or substituted 5-12 membered heteroaryl.

In one embodiment, $W^1$ is substituted by 0 to 4 substituents $R^a$. In one embodiment, $W^2$ is substituted by 0 to 4 substituents $R^b$. $R^a$ and $R^b$ are independently selected from the group consisting of halogen, —CN, —NO$_2$, —OR$^6$, —SR$^6$, —N(R$^6$)R$^7$, —C(O)NR$^6$R$^7$, —NR$^6$C(O)R$^7$, —S(O)$_2$R$^6$, —R$^6$SO$_2$NR$^7$, —R$^6$NR$^7$SO2, —C(O)R$^6$, —OC(O)NR$^6$, —NR$^6$C(O)NR$^7$, unsubstituted or substituted alkyl, unsubstituted or substituted alkenyl, and unsubstituted or substituted alkynyl. The substituents together with the atom(s) to which they are attached, may form an unsubstituted or substituted 3- to 12-membered ring, which contains 0-3 members selected from the group consisting of N, O, S, P(O), S(O), and S(O)$_2$.

In some embodiments, $W^1$ and $W^2$ are independently unsubstituted or substituted heteroaryl. The heteroaryl comprises 1-3 heteroatoms independently selected from the group consisting of O, N, P(O) and S(O)$_r$.

In some embodiments, $W^1$ is phenyl substituted with 0-4 substituents independently selected from the group consisting of halogen, —CN, —NO$_2$, —OR$^6$, —SR$^6$, —N(R$^6$)R$^7$, —C(O)NR$^6$R$^7$, —NR$^6$C(O)R$^7$, —S(O)$_2$R$^6$, —SO$_2$NR$^6$R$^7$, —R$^6$NSO$_2$R$^7$, —C(O)R$^6$, —OC(O)NR$^6$R$^7$, unsubstituted or substituted alkyl, unsubstituted or substituted alkenyl, and unsubstituted or substituted alkynyl.

Preferably, $W^1$ is phenyl substituted with 0-3 halogens.

In some embodiments, $W^2$ is substituted $C_{6-12}$ aryl or substituted heteroaryl. $W^2$ has 1 to 4 substituents independently selected from the group consisting of halogen, and —OR$^6$.

In some embodiments, $W^2$ is selected from the group consisting of unsubstituted or substituted phenyl, unsubstituted or substituted pyridyl, unsubstituted or substituted pyrazol, unsubstituted or substituted imidazol, unsubstituted or substituted pyrrol, tetrazol, unsubstituted or substituted oxazol, unsubstituted or substituted oxadiazol, unsubstituted or substituted thiazol, unsubstituted or substituted pyrimidyl, and unsubstituted or substituted naphthalenyl.

In one embodiment, L' is selected from the group consisting of a bond, —O—, —N(H)—, —S—, and unsubstituted or substituted alkyl. In one embodiment, $L^1$ is a bond.

In some embodiments, $L^2$ is selected from the group consisting of a bond, —O—, unsubstituted or substituted alkyl, —OR$^6$—, —NR$^6$—, —R$^6$N(R$^7$)—, —C(O)R$^6$—, —C(O)N(R$^6$)—, —NR$^6$C(O)R$^7$—, —NR$^6$C(O)NR$^7$—, —R$^6$S(O)$_2$—, unsubstituted or substituted $C_{6-12}$ aryl, and unsubstituted or substituted 3- to 12-membered heterocyclyl.

Preferably, $L^2$ is selected from the group consisting of a bond, unsubstituted or substituted phenyl, unsubstituted or substituted piperazinyl, and unsubstituted or substituted piperidinyl.

In one embodiment, Y is N. In another embodiment, Y is CR$^6$. In a preferred embodiment, Y is CH.

In one embodiment, $R^1$ is hydrogen.

In one embodiment, $R^2$ and $R^3$ are independently selected from the group consisting of hydrogen, and unsubstituted or substituted alkyl. Preferably, at least one of $R^2$ and $R^3$ is unsubstituted or substituted $C_{1-6}$ alkyl. Preferably, at least one of $R^2$ and $R^3$ is hydrogen. In one embodiment, $R^2$ is hydrogen, and $R^3$ is methyl.

In one embodiment, $R^4$ and $R^5$ are independently selected from the group consisting of unsubstituted or substituted alkyl, and —OR$^6$. In one embodiment, $R^4$ and $R^5$ are methyl. In one embodiment, $R^4$ and $R^5$ are —OH. In one embodiment, $R^4$ and $R^5$ are —OC$_2$H$_5$.

In some embodiments, —W$^2$-L$^2$-P(O)R$^3$R$^4$ is selected from the group consisting of:

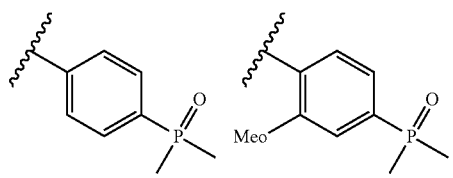

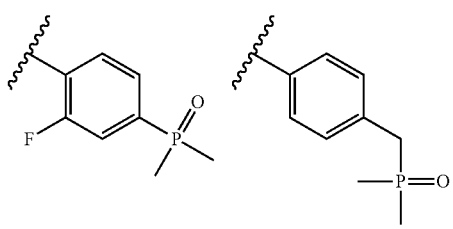

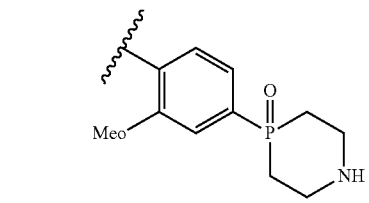

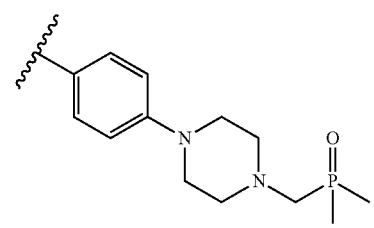

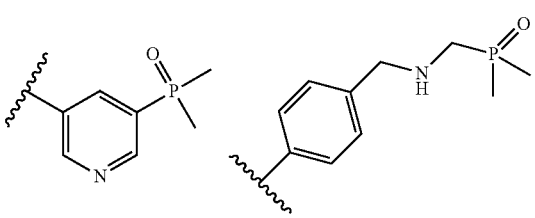

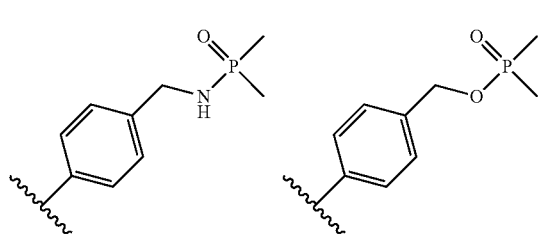

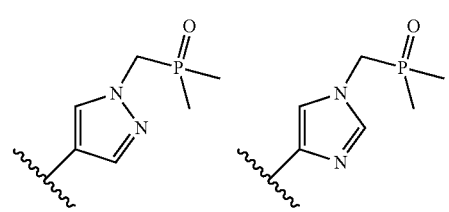

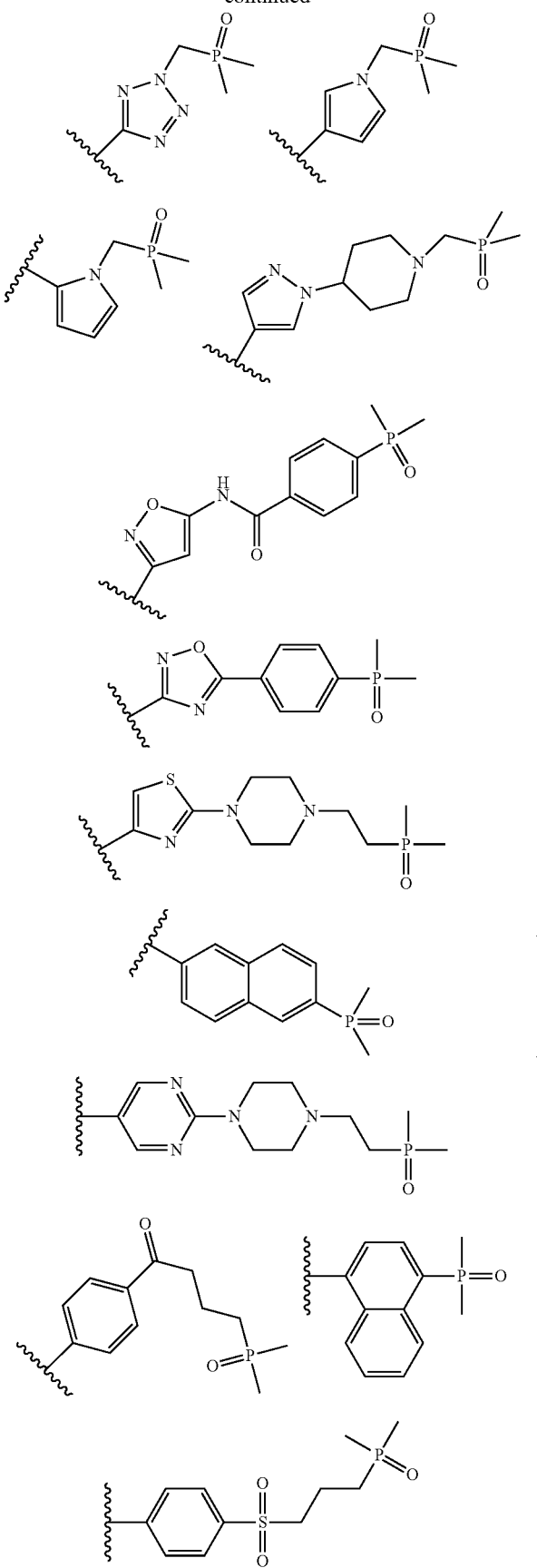

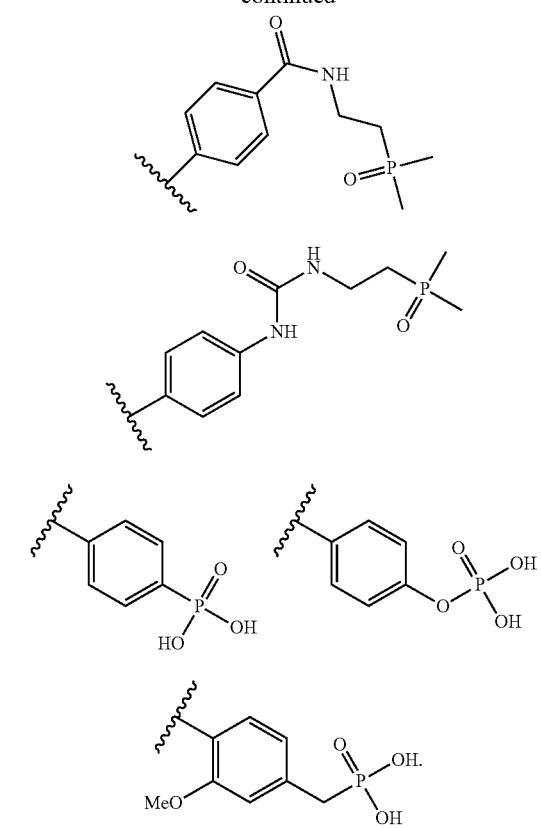

In one aspect, this invention relates to any of the specific phosphorus containing compounds delineated herein (e.g., as shown in the Examples 1-29).

In certain embodiments, when $L^1$ is a bond and $R^1$ is hydrogen, a compound is of formula (Ia):

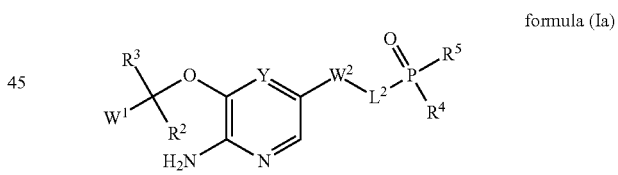

formula (Ia)

where $W^1$, $W^2$, $L^2$, Y, $R^2$, $R^3$, $R^4$ and $R^5$ are as defined above.

In certain embodiments, when $W_1$ is phenyl substituted with 1-3 $R^a$, $L_1$ is a bond, Y is CH, and $R_1$ and $R_2$ are hydrogen, the compound is of formula (Ib):

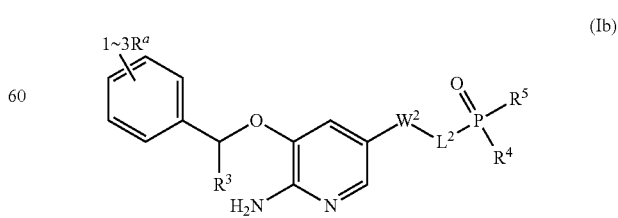

(Ib)

where $W^2$, $L^2$, $R^3$, $R^4$ and $R^5$ are as defined above.

In certain embodiments, the compound is of formula (Ic):

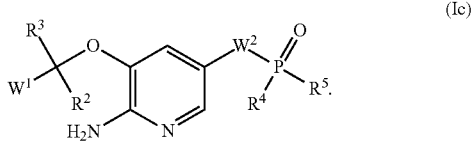

Where $W^1$ is $C_{6-12}$ aryl substituted with three substituents; $W^2$ is selected from the group consisting of unsubstituted or substituted $C_{6-12}$ aryl, and unsubstituted or substituted 3- to 12-membered heteroaryl;
$R^1$ is hydrogen;
$R^2$ and $R^3$ are independently selected from the group consisting of hydrogen, and unsubstituted or substituted alkyl; and $R^4$ and $R^5$ are independently selected from the group consisting —$OR^6$, and unsubstituted or substituted alkyl, wherein $R^6$ is selected from the group consisting of hydrogen, halogen, and unsubstituted or substituted $C_{1-12}$ alkyl.

In one embodiment, $R^a$ is halogen. Preferably, $R^a$ is chloro or fluoro.

In one embodiment, $R^3$ is selected from the group consisting of hydrogen, unsubstituted or substituted alkyl, and unsubstituted or substituted cycloalkyl. In one embodiment, $R^3$ is methyl.

In one embodiment, $R^4$ and $R^5$ are independently selected from the group consisting of unsubstituted or substituted alkyl, and —$OR^6$. Preferably, $R^4$ and $R^5$ are methyl, —OH, or —$OC_2H_5$.

In one embodiment, $W^2$ is selected from the group consisting of unsubstituted or substituted phenyl, unsubstituted or substituted pyridyl, unsubstituted or substituted pyrazol, unsubstituted or substituted imidazol, unsubstituted or substituted pyrrol, tetrazol, unsubstituted or substituted oxazol, unsubstituted or substituted oxadiazol, unsubstituted or substituted thiazol, unsubstituted or substituted pyrimidyl, and unsubstituted or substituted naphthalenyl.

In one embodiment, $L^2$ is selected from the group consisting of a bond, —O—, unsubstituted or substituted alkyl, —$OR^6$—, —$NR^6$—, —$C(O)R^6$—, —$C(O)N(R^6)$—, —$R^6S(O)_2$—, unsubstituted or substituted $C_{6-12}$ aryl, and unsubstituted or substituted 3- to 12-membered heterocyclyl.

In one embodiment, $L^2$ is selected from the group consisting of a bond, unsubstituted or substituted phenyl, unsubstituted or substituted piperazinyl, and unsubstituted or substituted piperidinyl.

In one embodiment, the present disclosure provides a compound selected from the group consisting of 3-[1-(2,6-dichloro-3-fluoro-phenyl)ethoxy]-5-(4-dimethylphosphorylphenyl)pyridin-2-amine; 3-[1-(2,6-dichloro-3-fluoro-phenyl)ethoxy]-5-[1-[1-(dimethylphosphorylmethyl)-4-piperidyl]pyrazol-4-yl]pyridin-2-amine; 3-[1-(2,6-dichloro-3-fluoro-phenyl)ethoxy]-5-[1-(dimethylphosphorylmethyl)pyrazol-4-yl]pyridin-2-amine; 5-[4-[(bis(dimethylphosphorylmethyl)amino)methyl]phenyl]-3-[1-(2,6-dichloro-3-fluoro-phenyl)ethoxy]pyridin-2-amine; 3-[1-(2,6-dichloro-3-fluoro-phenyl)ethoxy]-5-[4-[(dimethylphosphorylmethylamino)methyl]phenyl]pyridin-2-amine; 3-[1-(2,6-dichloro-3-fluoro-phenyl)ethoxy]-5-(5-dimethylphosphoryl-3-pyridyl)pyridin-2-amine; 3-[1-(2,6-dichloro-3-fluoro-phenyl)ethoxy]-5-[4-(dimethylphosphoryloxymethyl)phenyl]pyridin-2-amine; 3-[1-(2,6-dichloro-3-fluoro-phenyl)ethoxy]-5-(4-dimethylphosphoryl-2-methoxy-phenyl)pyridin-2-amine; 3-[1-(2,6-dichloro-3-fluoro-phenyl)ethoxy]-5-(4-dimethylphosphoryl-1-naphthyl)pyridin-2-amine; 3-[1-(2,6-dichloro-3-fluoro-phenyl)ethoxy]-5-(4-dimethylphosphoryl-2-fluoro-5-methoxy-phenyl)pyridin-2-amine; 3-[1-(2,6-dichloro-3-fluoro-phenyl)ethoxy]-5-(4-dimethylphosphorylphenyl)pyrazin-2-amine; 3-[1-(2,6-dichloro-3-fluoro-phenyl)ethoxy]-5-(4-dimethylphosphoryl-3-methoxy-phenyl)pyridin-2-amine; 3-[1-(2,6-dichloro-3-fluoro-phenyl)ethoxy]-5-(4-dimethylphosphoryl-2-fluoro-phenyl)pyridin-2-amine; 3-[1-(2,6-dichloro-3-fluoro-phenyl)ethoxy]-5-(4-dimethylphosphoryl-3-fluoro-phenyl)pyridin-2-amine; 3-[1-(2,6-dichloro-3-fluoro-phenyl)ethoxy]-5-[4-dimethylphosphoryl-2-(trifluoromethyl)phenyl]pyridin-2-amine; 3-[1-(2,6-dichloro-3-fluoro-phenyl)ethoxy]-5-(6-dimethylphosphoryl-3-pyridyl)pyridin-2-amine, 2-[6-amino-5-[1-(2,6-dichloro-3-fluoro-phenyl)ethoxy]-3-pyridyl]-5-dimethylphosphoryl-phenol; 3-[1-(2,6-dichloro-3-fluoro-phenyl)ethoxy]-5-(5-dimethylphosphoryl-2-pyridyl)pyridin-2-amine; 5-(2-chloro-4-dimethylphosphoryl-phenyl)-3-[1-(2,6-dichloro-3-fluoro-phenyl)ethoxy]pyridin-2-amine; 3-[1-(2,6-dichloro-3-fluoro-phenyl)ethoxy]-5-[4-dimethylphosphoryl-2-(trifluoromethoxy)phenyl]pyridin-2-amine; 3-[1-(2,5-dichlorophenyl)ethoxy]-5-(4-dimethylphosphorylphenyl)pyridin-2-amine; 3-[1-(2-chloro-5-fluoro-phenyl)ethoxy]-5-(4-dimethylphosphorylphenyl)pyridin-2-amine; 3-[(1R)-1-(2,6-dichloro-3-fluoro-phenyl)ethoxy]-5-(4-dimethylphosphorylphenyl)pyridin-2-amine; 3-[(1R)-1-(2,6-dichloro-3-fluoro-phenyl)ethoxy]-5-(4-dimethylphosphoryl-2-methoxy-phenyl)pyridin-2-amine; 3-[(1R)-1-(2,6-dichloro-3-fluoro-phenyl)ethoxy]-5-(4-dimethylphosphoryl-2-fluoro-phenyl)pyridin-2-amine; 3-[1-2-(2-chloro-5-fluoro-phenyl)ethoxy]-5-(4-diethoxyphosphorylphenyl)pyridine-2-amine; [4-(6-amino-5-[1-(2-chloro-5-fluoro-phenyl)ethoxyl]-3-pyridyl]phenyl]phosphonic acid; 3-[(1R)-1-2-(2,6-dichloro-3-fluoro-phenyl)ethoxy]-5-(4-diethoxyphosphorylphenyl)pyridine-2-amine; and [4-(6-amino-5-[(1R)-1-(2,6-dichloro-3-fluoro-phenyl)ethoxyl]-3-pyridyl]phenyl]phosphonic acid.

In one aspect, this invention features a pharmaceutical composition, which includes a compound of formula (I) (including any subgenera or specific compounds thereof) or a salt (e.g., a pharmaceutically acceptable salt) or a prodrug thereof and a pharmaceutically acceptable adjuvant, carrier or diluent. In some embodiments, the composition can include an effective amount of the compound or the salt thereof. In some embodiments, the composition can further include an additional therapeutic agent.

In one aspect of the invention is directed to the use of any of the inventive compounds described herein in the preparation of a medicament, which is useful in the treatment of a disease mediated by ALK/cMet kinase activity, such as cancer.

The compounds described herein can be synthesized according to methods described herein (or variations thereof) and/or conventional, organic chemical synthesis methods from commercially available starting materials and reagents or from starting materials and reagents that can be prepared according to conventional organic chemical synthesis methods. The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternative sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

In some embodiments, the compounds described herein can be prepared according to Schemes 1-4, wherein, $R^1$ to $R^5$, $R^a$, $R^b$, $L^1$, $L^2$, $W^1$ and $W^2$ are selected from groups defined above. In a general way, a $P(O)R^4R^5$ group can be introduced onto an aryl or heteroaryl moiety by reaction of an aryl halide or heteroaryl halide (1) with $P(O)HR^4R^5$ in the presence of a palladium catalyst such as $Pd(PPh_3)_4$, $Pd_2(dba)_3$, and the like. Suitable solvents for use in the above process are THF, glyme, dioxane, dimethoxyethane, DMF, DMSO, MeCN, and the like. The above process can be carried out at temperatures between room temperature and 140° C. The above process is preferably carried out under reflux of MeCN.

In a typical preparation, a compound of bromide 2 can be reacted with a suitable coupling partner (bis(pinacolato)diboron or pinacolborane) in a suitable solvent under palladium catalysis to give boronic ester 3. Suitable solvents for use in this process are THF, glyme, dioxane, dimethoxyethane, DMF, DMSO, MeCN, and the like. If desired, mixtures of these solvents can be used; however, a preferred solvent is dioxane. The above process can be carried out at temperatures between room temperature and 140° C. The above process is preferably carried out at about atmospheric pressure although higher or lower pressures can be used.

In a typical preparation of compounds of Formula I, a compound of formula 4 is reacted with a suitable boronic ester (Scheme 1) in a suitable solvent via typical Suzuki coupling procedures. Suitable solvents for use in the above process include THF, dioxane, dimethoxyethane, DMF, MeCN, MeOH, EtOH, isopropanol, dichloromethane, chloroform, and the like. If desired, mixtures of these solvents can be used; however, preferred solvents are dimethoxyethane/water. The above process can be carried out at temperatures between 0° C. and 120° C. Preferably, the reaction is carried out under reflux of dimethoxythane/water. The Suzuki coupling is preferably carried out under nitrogen atmosphere. Alternatively, phosphine oxide 7 can be prepared by reacting $PH(O)R^4R^5$ with boronic acid 6 as outlined above and compound 5 can be prepared by a coupling reaction between boronic acid 7 and bromide 4 under the standard Suzuki coupling conditions. If compound 5 is phosphonate ester, the corresponding acid is obtained by hydrolysis of the ester. The phosphonate ester groups may be cleaved by using bromotrimethylsilane (BTMS) or iodotrimethylsilane (ITMS) in a polar solvent such as dichloromethane. The above process can be carried out at temperatures between 0° C. and 60° C.

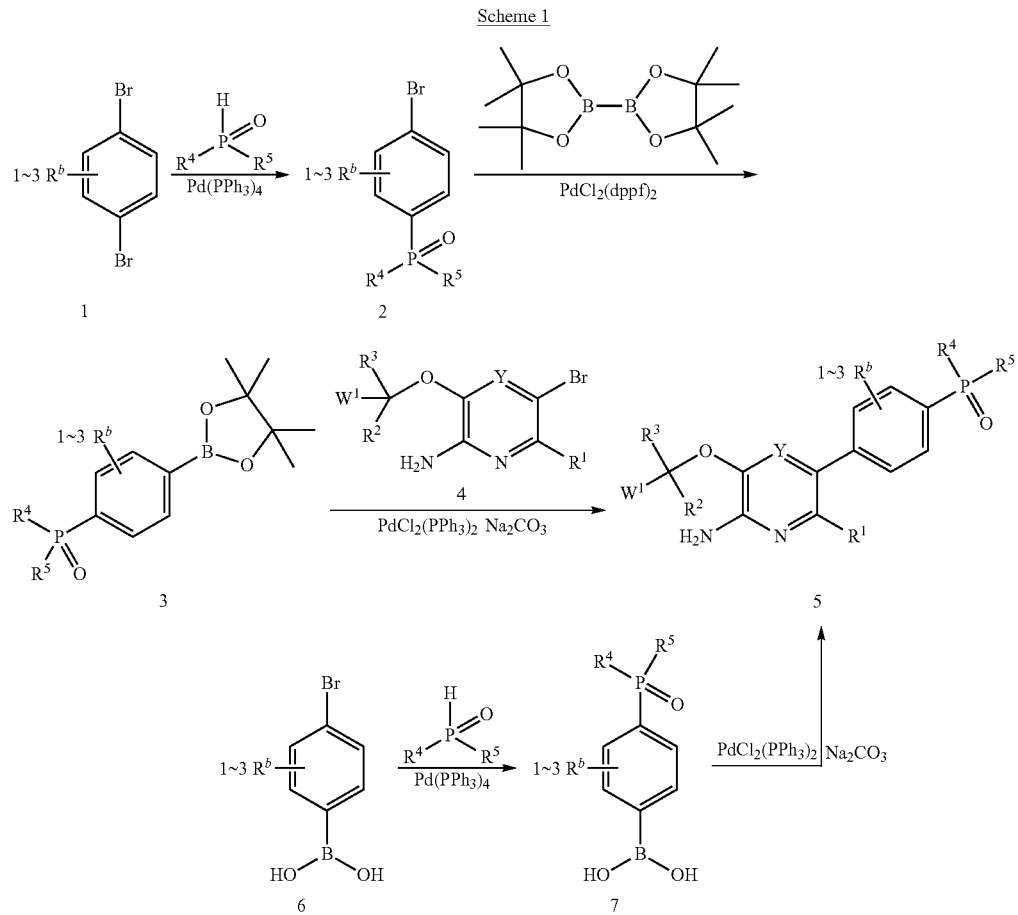

Scheme 1

As shown in Scheme 2, amides of formula 10 can be prepared by reacting of amine 8 with chloride of formula 9. The reaction can be carried out in inert organic solvents such as methylene chloride, acetonitrile, dimethylformamide, tetrahydrofuran, dioxane, and the like. The reaction is typically carried out in the presence of a suitable base such as diisopropylethylamine, triethylamine, N-methylmorpholine, and the like. Similarly, phosphinates 12 can be prepared by reacting alcohol 11 with 9 in inert organic solvents such as methylene chloride, acetonitrile, dimethylformamide, tetrahydrofuran, dioxane, and the like. The reaction is typically also carried out in the presence of a suitable base such as diisopropylethylamine, triethylamine, N-methylmorpholine, and the like.

lated compounds of formula 14 and/or dialkylated compounds of formula 15. Alternatively, alkylation of pyrazole 16 with alkylating agent 13 gives the compounds of formula 17. The alkylation reaction can be carried out in inert organic solvents such as methylene chloride, acetonitrile, dimethylformamide, tetrahydrofuran, dioxane, and the like. The reaction is typically carried out in the presence of a suitable base such as diisopropylethylamine, triethylamine, N-methylmorpholine, potassium carbonate, sodium hydride, and the like.

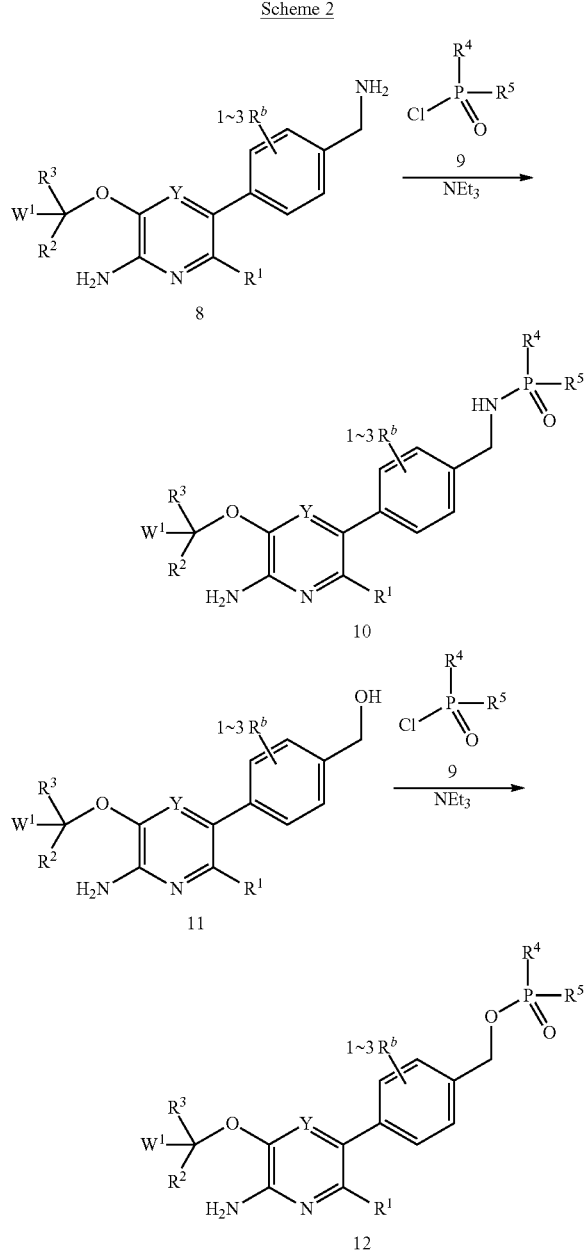

Scheme 2

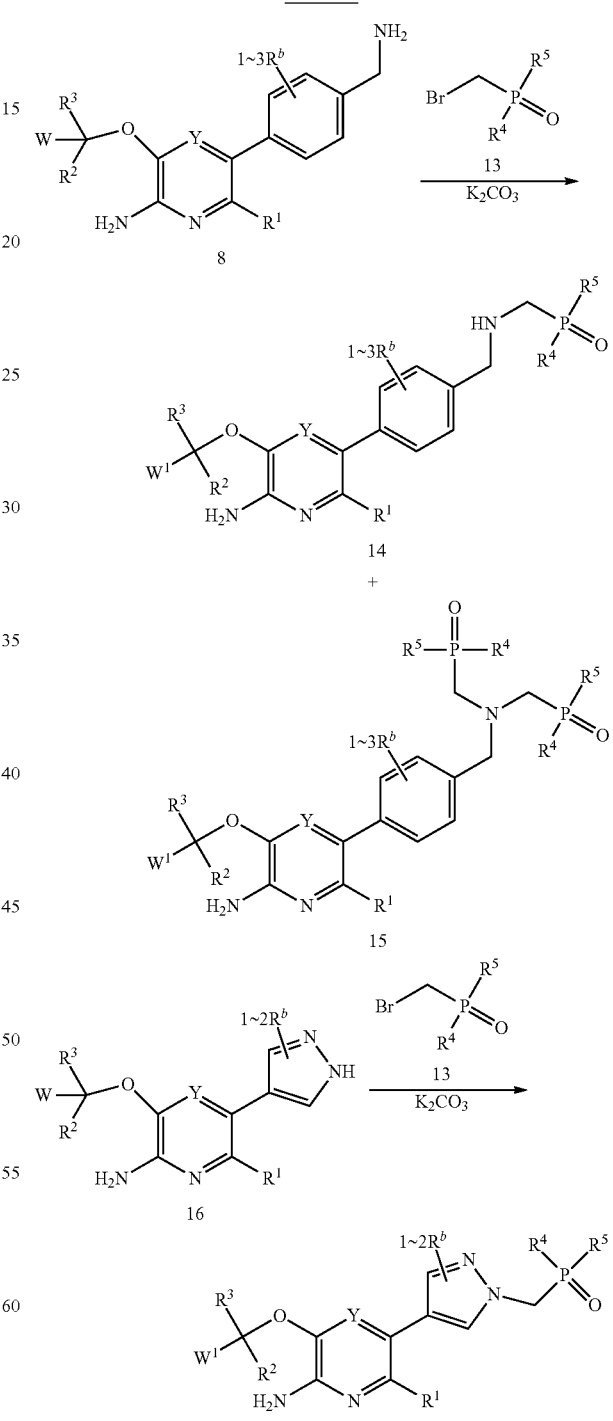

Scheme 3

According to Scheme 3, compounds of formula 14, 15 and 17 can be prepared by an alkylation process. Alkylation of amine 8 with an alkylating agent 13 provides the mono alky- The bromide 4 can be prepared as shown in Scheme 4. Nitration of compound 18 at 0~25° C. can give the mono nitration product 19. The OH of formula 19 and a benzyl alcohol can be reacted with triphenylphosphine ($PPh_3$) and diisopropylazodicarboxylate (DIAD) to form the ether of formula 20. Reduction of 20 in the presence of iron metal can provide the anilines 4.

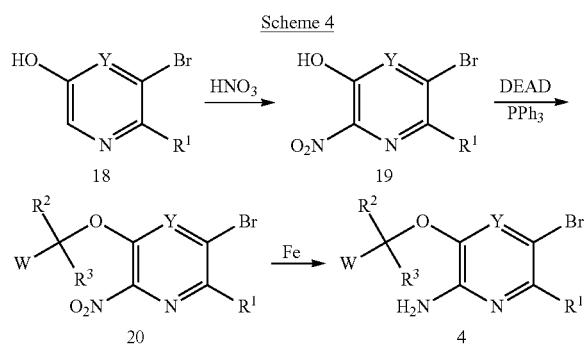

Scheme 4

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The term "pharmaceutically acceptable carrier or adjuvant" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In general, the compounds described herein can be used for, e.g., treating, inhibiting, controlling, relieving, ameliorating, preventing, delaying the onset of, or reducing the risk of developing one or more diseases, disorders, conditions or symptoms mediated by PT kinases.

ALK Enzyme Activity Assay:

ALK kinase was purchased from Millipore Company (Billerica, Mass., USA). HTRF®KinEASET™ was purchased from Cisbio Company (Bedford, Mass., USA). The assay was conducted according to the procedure provided in the assay kit. In brief, incubation was carried out in the kinase buffer containing ALK (0.3 ng/μL), ATP (25 μM), TK substrate-biotin (10 μM), DTT (1 mM), $MgCl_2$ (5 mM), $MnCl_2$ (5 mM) in the presence of the tested articles at various concentrations in 384-well plate at 30° C. for 30 minutes. The reaction was stopped by addition of Sa-XL665 in EDTA solution, and the phosphorylated substrate was detected with a proprietary phospho-specific monoclonal antibody labeled with $Eu^{3+}$-Cryptate and a proprietary biotinylated kinase substrate detected using XL665 labeled streptavidin. $IC_{50}$ value was calculated using median-effect method (Chou 2006). The $IC_{50}$ value for the example compounds is shown in Table 1.

The activities of ALK wild type, its mutant F1174L, R1275Q, L1196M and EML4-ALK, NPM1-ALK were also determined using off-chip mobility shift assay at Carna Biosciences (Chuo-ku, Kobe, Japan). In brief, 5 μL of ×4 compound solution, 5 μL of ×4 substrate/ATP/metal solution and 10 μL of ×2 kinase solution were prepared with assay buffer (20 mM HEPES, 0.01% Triton X-100, 2 mM DTT, pH 7.5) and mixed and incubated in a well of polypropylene 384 well microplate for 1 or 5 hours (depending on the enzyme). The ATP concentration used in the reaction was 50 μM for ALK wild type, F1174L mutant, EML4-ALK and NPM1-ALK, and 100 μM for R1275Q and 72 μM for L1196M. An aliquot of 60 μL of termination buffer (QuickScout Screening Assist MSA, Carna Biosciences) was added to each well to terminate the reactions. The reaction mixture was applied to Lab-Chip3000 system (Caliper Life Science), and the product and substrate peptide peaks were separated and quantitated. The kinase reaction was evaluated by the product ratio calculated from peak heights of product (P) and substrate (S) peptides (P/(P+S)). IC50 value was calculated from concentration vs. % Inhibition curves by fitting to a four parameter logistic curve. The $IC_{50}$ value for examples 24 and 25 was less than 0.05 μM for ALK wild type, its mutant F1174L, R1275Q, L1196M and EML4-ALK, NPM1-ALK.

TABLE 1

$IC_{50}$ Values for inhibition of ALK kinase activity and proliferation of cancer cell line Karpas299, SU-DHL-1 and H2228*

| Example | ALK Kinase | Karpas299 | SU-DHL-1 | H2228 |
|---|---|---|---|---|
| 1 | B | B | A | A |
| 2 | A | N/A | N/A | D |
| 3 | B | N/A | N/A | N/A |
| 4 | B | N/A | N/A | D |
| 5 | B | N/A | D | B |
| 6 | B | N/A | D | B |
| 7 | B | N/A | N/A | N/A |
| 8 | A | A | A | A |
| 9 | D | N/A | N/A | N/A |
| 10 | D | N/A | N/A | N/A |
| 11 | B | N/A | B | N/A |
| 12 | A | N/A | N/A | N/A |
| 13 | A | A | B | N/A |
| 14 | D | N/A | D | N/A |
| 15 | C | N/A | N/A | N/A |
| 16 | C | N/A | D | N/A |
| 17 | B | N/A | A | N/A |
| 18 | B | B | B | N/A |
| 19 | B | N/A | B | N/A |
| 20 | C | N/A | B | N/A |
| 21 | B | N/A | A | N/A |
| 22 | B | N/A | A | N/A |
| 23 | B | A | A | A |
| 24 | A# | A | A | A |
| 25 | A# | A | A | A |
| 26 | C | N/A | N/A | N/A |
| 27 | A | N/A | D | N/A |
| 28 | B | N/A | D | N/A |
| 29 | A | N/A | D | N/A |

*A for $IC_{50}$<0.1 μM; B for $IC_{50}$>0.1 μM~0.5 μM; C for $IC_{50}$>0.5 μM~1.0 μM; D for for $IC_{50}$>1 μM~5 μM;
N/A; not available;
for ALK wild type, its mutant F1174L, R1275Q, L1196M and EML4-ALK, NPM1-ALK.

Cell Proliferation Assay:

Karpas299 and SU-DHL-1 cells were purchased from Deutsche Sammlung von Mikroorganismen and Zellkulturen (Germany). H2228 was purchased from American Type Culture Collection (USA). All cells were cultured in the recommended medium and serum concentration. Cells were maintained at 37° C. in a humidified atmosphere with 5% $CO_2$. For ALK kinase phosphorylation, cells were seeded in 96-well plates overnight in medium supplemented with 10% fetal bovine serum (PBS). After 24 hours, the medium was removed and cells were cultured in serum-free medium at 37° C. in the presence of various concentrations of the test articles for 1 hour. After incubation with the tested articles, cells were washed once with HBSS supplemented with 1 mM $Na_3VO_4$ and protein lysates were generated. Subsequently, phosphorylation of ALK was assessed by a sandwich ELISA method using an immobilized anti-total-ALK antibody and an anti-phospho-ALK antibody (pY1604) as a detection antibody. $IC_{50}$ value was calculated using median-effect method. (Chou 2006). For the inhibition of ALK phosphorylation, the examples 1, 8, 23, 24 and 25 showed $IC_{50}$ value of <0.1 μM in Karpas299 cells, the examples 8, 23, 24 and 25 showed $IC_{50}$ value of <0.05 μM in SU-DHL-1 cells, and the examples 23, 24, 25 showed $IC_{50}$ value of <0.05 μM and the examples 1 and 2 had $IC_{50}$ value of <0.5 μM.

For cell proliferation assay, cells were seeded in 96-well pates at low density at 37° C. in medium supplemented with 10% FBS and after 24 hours were switched to low serum medium (2% FBS). Cells were further incubated in the presence of the test articles at various concentrations at 37° C. for 72 hours. Two assays were employed to determine the relative cell numbers. One is a 3-(4,5-dimethylthiazol-2-yl)-5-(3-carboxymethoxyphenyl)-2-(4-sulfophenyl)-2H-tetrazolium (MTS) assay using a CellTiter 96® Aqueous Non-Radioactive Cell Proliferation kit (Promega), and the other is a BrdU incorporation assay using a DELFIA® Cell Proliferation Kit (Perkin Elmer). $IC_{50}$ value was calculated using median-effect method (Chou 2006). The $IC_{50}$ value for the example compounds is shown in Table 1.

Pharmacokinetic Assay:

The tested articles were given to Sprague-Dawley rats or beagle dogs by intravenous and oral administration. Plasma samples were prepared from blood samples which were collected at various time points. The plasma concentrations of the tested articles were determined by specific LC-MS/MS analytical methods. Pharmacokinetic parameters were calculated with WinNonlin®. Examples 1, 8 and 13 had an oral bioavailabilty>20% and $t_{1/2}$>3 hours after oral administration in rats or dogs.

Xenograft Studies:

Xenograft model was developed in athymic mice (nude/nud mouse) with lung cancer cell line H2228 purchased from the American Type Culture Collection Company (Manassas, Va., USA). In brief, H2228 cells ($1 \times 10^7$) were implanted s.c. into the hind flank region of each mouse and allowed to grow to the designated size (c.a. 150-200 $mm^3$) before administration of the tested articles. The tested articles were given orally at various dose levels twice daily for 10-14 days. Tumor volume and body weight were measured during the experiments. Tumor regression values were determined using the standard approach.

Examples 24 and 25 reduced the tumor size by approximately 80% following 14 days oral dosing at 60 mg/kg (BID). The tumor disappeared in some animals. The inhibition of tumor growth compared to the vehicle control was 79% and 93% for example 24 at 20 and 60 mg/kg, 46%, 73% and 93% for example 25 at 6, 20 and 60 mg/kg, respectively.

EXAMPLES OF COMPOUNDS

Compounds of the disclosure can be prepared using conventional synthetic methodology. Examples of approaches that may be taken to synthesize these compounds are shown below. Nonetheless, one skilled in the art will recognize that alternative methods may be employed to synthesize the target compounds of this disclosure, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the invention.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

3-[1-(2,6-dichloro-3-fluoro-phenyl)ethoxy]-5-(4-dimethylphosphorylphenyl)pyridin-2-amine

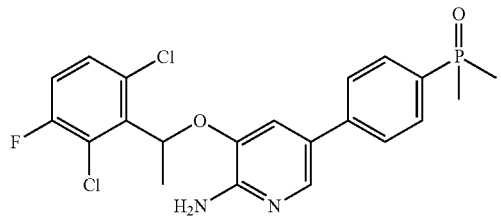

Step 1: Synthesis of (4-brom-phenyl)-dimethyl-phosphinoxide

A solution of 1,4-dibromobenzene (2.35 g, 10 mmol), dimethylphosphine oxide (0.78 g, 10 mmol), and tetrakis(triphenylphosphine) palladium (0) (0.5 g) in nitrogen-purged $CH_3CN$ (20 mL) and triethylamine (5 mL) was heated at reflux for overnight. Then, the reaction mixture was concentrated and the residue was chromatographed on silica gel (0~20 percent MeOH/DCM) to afford the product (600 mg, 26%) as a colorless solid; $^1H$ NMR ($CD_3OD$): δ 7.80-7.70 (m, 4H), 1.75 (d, 6H).

Step 2: Synthesis of [2-[4-(Dimethylphosphoryl)phenyl]-4,4,5,5-tetramethyl-1,3,2-dioxaborolane A 50 mL flask was charged with (4-brom-phenyl)-dimethyl-phosphinoxide (0.46 g, 2.0 mmol), bis(pinacolato)diboron (1.10 g, 4.0 mmol), KOAc (1.0 g, 10.6 mmol) and $PdCl_2(dppf)$ $CH_2Cl_2$ complex (206 mg, 0.26 mmol) under nitrogen. Dry 1,4-dioxane (10 mL) was added and the mixture was heated at 90° C. for overnight. The reaction mixture was cooled, filtered over celite, and the solvent was removed. A quarter of the residue was used for the next reaction without further purification.

Step 3: A mixture of the boronic ester from step 2,5-bromo-3-[(2,6-dichloro-3-fluoro-phenyl)-ethoxy]-pyridin-2-ylamine (0.19 g, 0.5 mmol), dichlorobis(triphenylphosphine) palladium(II) (150 mg, 0.21 mmol), DME (20 mL), water (5 mL), and $Na_2CO_3$ (0.4 g) was de-gassed for 10 minutes with nitrogen and then heated to reflux. After 2 hours, the reaction was cooled to room temperature. EtOAc (80 mL) and water (80 mL) were added. The organic layer was separated, dried over $Na_2SO_4$, and concentrated. The product was purified by HPLC (water/methanol, 10~100%) to afford 105 mg of the title compound as a white solid (46%). ESMS: m/z 453 $(M+H)^+$.

Example 2

3-[1-(2,6-dichloro-3-fluoro-phenyl)ethoxy]-5-[1-[1-(dimethylphosphorylmethyl)-4-piperidyl]pyrazol-4-yl]pyridin-2-amine

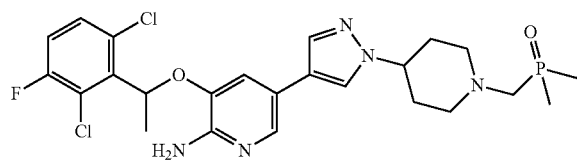 [SMILES: CC(Oc1cc(-c2cnn(C3CCN(CP(C)(C)=O)CC3)c2)cnc1N)c1c(Cl)ccc(F)c1Cl]

A mixture of 3-(1-(2,6-dichloro-3-fluoro-phenyl)ethoxy)-5-(1-piperidin-4-yl-1H-pyrazol-4-yl)-pyridin-2-amine (6 mg, 0.013 mmol), chloromethyl-dimethyl-phosphine oxide (100 mg, 0.79 mmol), and potassium carbonate (0.2 g) in DMF (5 mL) was heated at 80° C. overnight. The solid was removed and the residue was purified by HPLC (water/methanol, 10~100%) to give the title compound as an off-white solid (3 mg, 40%); ESMS: m/z 540 $(M+H)^+$.

Example 3

3-[1-(2,6-dichloro-3-fluoro-phenyl)ethoxy]-5-[1-(dimethylphosphorylmethyl)pyrazol-4-yl]pyridin-2-amine

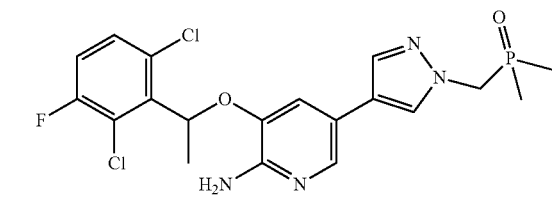 [SMILES: CC(Oc1cc(-c2cnn(CP(C)(C)=O)c2)cnc1N)c1c(Cl)ccc(F)c1Cl]

The title compound was prepared from 3-[1-(2,6-dichloro-3-fluoro-phenyl)-ethoxy]-5-(1H-pyrazol-4-yl)-pyridin-2-ylamine and chloromethyl-dimethyl-phosphine oxide following the same procedure as Example 2. ESMS: m/z 457 $(M+H)^+$.

Example 4

5-[4-[(bis(dimethylphosphorylmethyl)amino)methyl]phenyl]-3-[1-(2,6-dichloro-3-fluoro-phenyl)ethoxy]pyridin-2-amine

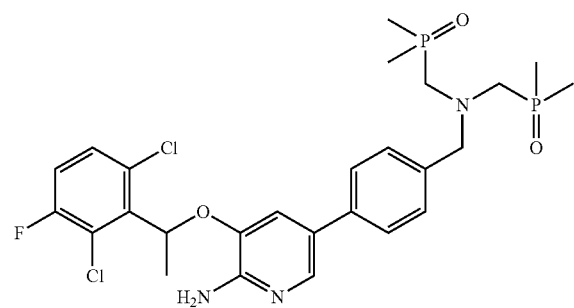 [SMILES: CC(Oc1cc(-c2ccc(CN(CP(C)(C)=O)CP(C)(C)=O)cc2)cnc1N)c1c(Cl)ccc(F)c1Cl]

Step 1: 5-[4-(aminomethyl)phenyl]-3-[1-(2,6-dichloro-3-fluoro-phenyl)ethoxy]pyridin-2-amine was prepared from 5-bromo-3-[(2,6-dichloro-3-fluoro-phenyl)-ethoxy]-pyridin-2-ylamine and 4-(aminomethyl)phenyl boronic acid following the same procedure as Example 1 Step 3 as an off-white solid, ESMS: m/z 406 (M+H)$^+$.

Step 2: the title compound (di-alkylation product) was prepared from 5-[4-(aminomethyl)phenyl]-3-[1-(2,6-dichloro-3-fluoro-phenyl)ethoxy]pyridin-2-amine and chloromethyl-dimethyl-phosphine oxide following the same procedure as Example 2. ESMS: m/z 584 (M+H)$^+$.

Example 5

3-[1-(2,6-dichloro-3-fluoro-phenyl)ethoxy]-5-[4-[(dimethylphosphorylmethylamino)methyl]phenyl]pyridin-2-amine

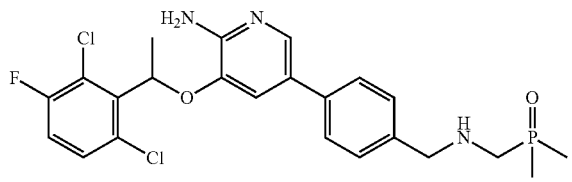 [SMILES: CC(Oc1cc(-c2ccc(CNCP(C)(C)=O)cc2)cnc1N)c1c(Cl)ccc(F)c1Cl]

The title compound (mono alkylation product) was also isolated from Example 4 Step 2; ESMS: m/z 496 (M+H)$^+$.

Example 6

3-[1-(2,6-dichloro-3-fluoro-phenyl)ethoxy]-5-(5-dimethylphosphoryl-3-pyridyl)pyridin-2-amine

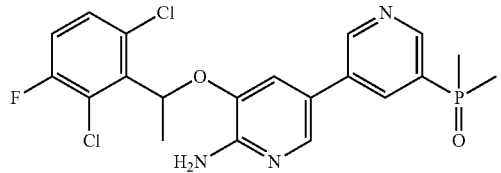 [SMILES: CC(Oc1cc(-c2cncc(P(C)(C)=O)c2)cnc1N)c1c(Cl)ccc(F)c1Cl]

The title compound was prepared from 5-bromo-3-[(2,6-dichloro-3-fluoro-phenyl)-ethoxy]-pyridin-2-ylamine, 3-bromo-5-(4,4,5,5-tetramethyl-1,3,2-dioxaborolan-2-yl)pyridine, and dimethylphosphine oxide following the same procedures as Example 1 Step 1 and Step 3; ESMS: m/z 454 (M+H)$^+$.

Example 7

3-[1-(2,6-dichloro-3-fluoro-phenyl)ethoxy]-5-[4-(dimethylphosphoryloxymethyl)phenyl]pyridin-2-amine

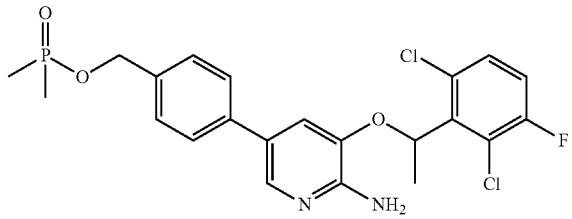 [SMILES: CC(Oc1cc(-c2ccc(COP(C)(C)=O)cc2)cnc1N)c1c(Cl)ccc(F)c1Cl]

Step 1: [4-[6-amino-5-[1-(2,6-dichloro-3-fluoro-phenyl)ethoxy]-3-pyridyl]phenyl]methanol was prepared from 5-bromo-3-[(2,6-dichloro-3-fluoro-phenyl)-ethoxy]-pyridin-2-ylamine and 4-(hydroxymethyl)phenyl boronic acid followed the same procedure as Example 1 Step 3 as an off-white solid. ESMS: m/z 407 (M+H)$^+$.

Step 2: a mixture of [4-[6-amino-5-[1-(2,6-dichloro-3-fluoro-phenyl)ethoxy]-3-pyridyl]phenyl]methanol (15 mg, 0.037 mmol), dimethylphosphoryl chloride (50 mg, 0.45 mmol), and triethylamine (0.5 mL) in dichloromethane (10 mL) was stirred at room temperature for 1.5 hours. The solvent was removed and the residue was purified by HPLC (water/methanol, 10~100%) to give the title compound (2 mg, 11%). ESMS: m/z 483 (M+H)$^+$.

Example 8

3-[1-(2,6-dichloro-3-fluoro-phenyl)ethoxy]-5-(4-dimethylphosphoryl-2-methoxy-phenyl)pyridin-2-amine

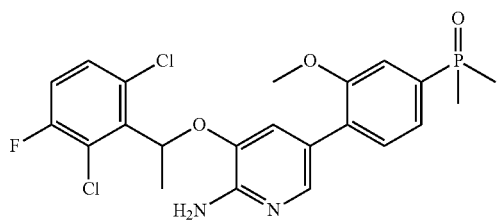 [SMILES: COc1cc(P(C)(C)=O)ccc1-c1cnc(N)c(OC(C)c2c(Cl)ccc(F)c2Cl)c1]

The title compound was prepared from 5-bromo-3-[1-(2,6-dichloro-3-fluoro-phenyl)-ethoxy]-pyridin-2-ylamine, 4-bromo-2-methoxyphenylboronic acid, and dimethylphosphine oxide following the same procedures as Example 1 Step 1 and Step 3; ESMS: m/z 483 (M+H)$^+$.

Example 9

3-[1-(2,6-dichloro-3-fluoro-phenyl)ethoxy]-5-(4-dimethylphosphoryl-1-naphthyl)pyridin-2-amine

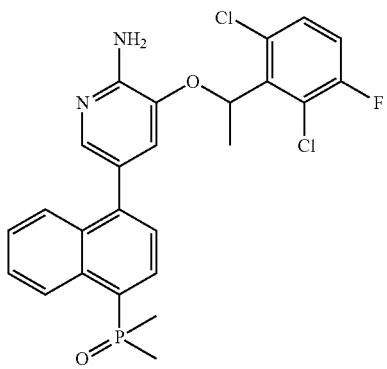 [SMILES: CC(Oc1cc(-c2ccc(P(C)(C)=O)c3ccccc23)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 1-bromo-4-(dihydroxyboryl)naphthalene, and dimethylphosphine oxide following the same procedures as Example 1 Step 1 and Step 3. ESMS: m/z 503 (M+H)$^+$.

Example 10

3-[1-(2,6-dichloro-3-fluoro-phenyl)ethoxy]-5-(4-dimethylphosphoryl-2-fluoro-5-methoxy-phenyl)pyridin-2-amine

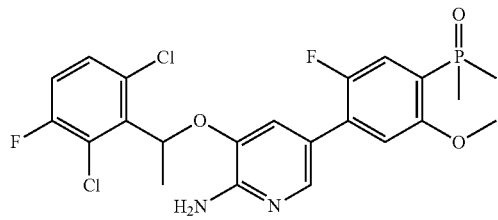 [SMILES: COc1cc(-c2cnc(N)c(OC(C)c3c(Cl)ccc(F)c3Cl)c2)c(F)cc1P(C)(C)=O]

The title compound was prepared from 5-bromo-3-[1-(2,6-dichloro-3-fluoro-phenyl)-ethoxy]-pyridin-2-ylamine, 4-bromo-2-fluoro-5-methoxyphenylboronic acid, and dimethylphosphine oxide following the same procedures as Example 1 Step 1 and Step 3. ESMS: m/z 501 (M+H)$^+$.

Example 11

3-[1-(2,6-dichloro-3-fluoro-phenyl)ethoxy]-5-(4-dimethylphosphorylphenyl)pyrazin-2-amine

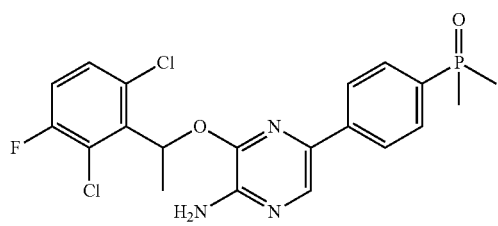

The title compound was prepared from 5-bromo-3-[1-(2,6-dichloro-3-fluoro-phenyl)-ethoxy]-pyrazin-2-ylamine, 4-bromophenylboronic acid, and dimethylphosphine oxide following the same procedures as Example 1 Step 1 and Step 3; ESMS: m/z 454 (M+H)$^+$.

Example 12

3-[1-(2,6-dichloro-3-fluoro-phenyl)ethoxy]-5-(4-dimethylphosphoryl-3-methoxy-phenyl)pyridin-2-amine

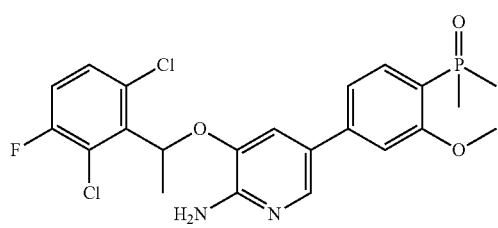 [SMILES: COc1cc(-c2cnc(N)c(OC(C)c3c(Cl)ccc(F)c3Cl)c2)ccc1P(C)(C)=O]

The title compound was prepared from 5-bromo-3-[1-(2,6-dichloro-3-fluoro-phenyl)-ethoxy]-pyridin-2-ylamine, 4-bromo-3-methoxyphenyl boronic acid, and dimethylphosphine oxide following the same procedures as Example 1 Step 1 and Step 3; ESMS: m/z 483 (M+H)$^+$.

Example 13

3-[1-(2,6-dichloro-3-fluoro-phenyl)ethoxy]-5-(4-dimethylphosphoryl-2-fluoro-phenyl)pyridin-2-amine

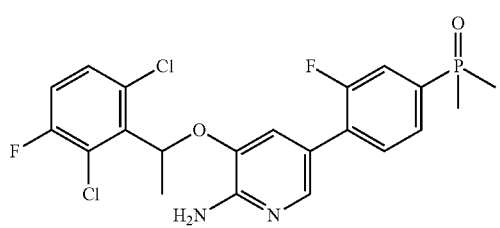

The title compound was prepared from 5-bromo-3-[1-(2,6-dichloro-3-fluoro-phenyl)-ethoxy]-pyridin-2-ylamine, 4-bromo-2-fluoro-phenyl boronic acid, and dimethylphosphine oxide following the same procedures as Example 1 Step 1 and Step 3; ESMS: m/z 471 (M+H)$^+$.

Example 14

3-[1-(2,6-dichloro-3-fluoro-phenyl)ethoxy]-5-(4-dimethylphosphoryl-3-fluoro-phenyl)pyridin-2-amine

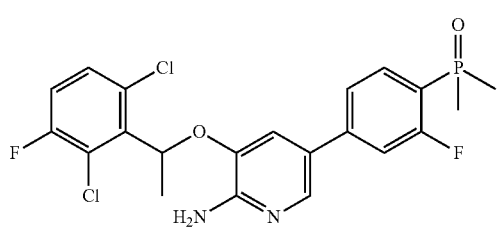 [SMILES: CC(Oc1cc(-c2ccc(P(C)(C)=O)c(F)c2)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 4-bromo-3-fluoro-phenyl boronic acid, and dimethylphosphine oxide following the same procedures as Example 1 Step 1 and Step 3; ESMS: m/z 471 (M+H)$^+$.

Example 15

3-[1-(2,6-dichloro-3-fluoro-phenyl)ethoxy]-5-[4-dimethylphosphoryl-2-(trifluoromethyl)phenyl]pyridin-2-amine

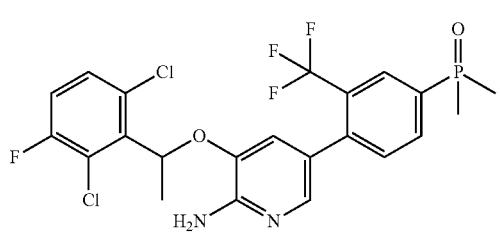 [SMILES: CC(Oc1cc(-c2ccc(P(C)(C)=O)cc2C(F)(F)F)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 4-bromo-2-trifluoromethyl-phenyl boronic acid, and dimethylphosphine oxide following the same procedures as Example 1 Step 1 and Step 3; ESMS: m/z 521 (M+H)$^+$.

Example 16

3-[1-(2,6-dichloro-3-fluoro-phenyl)ethoxy]-5-(6-dimethylphosphoryl-3-pyridyl)pyridin-2-amine

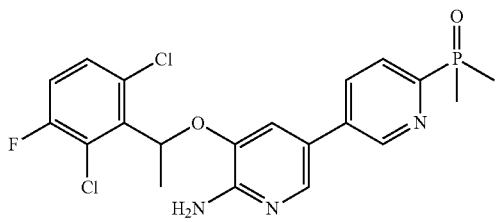 [SMILES: CC(Oc1cc(-c2ccc(P(C)(C)=O)nc2)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 6-bromo-3-pyridinylboronic acid, and dimethylphosphine oxide following the same procedures as Example 1 Step 1 and Step 3; ESMS: m/z 454 (M+H)$^+$.

Example 17

2-[6-amino-5-[1-(2,6-dichloro-3-fluoro-phenyl)ethoxy]-3-pyridyl]-5-dimethylphosphoryl-phenol

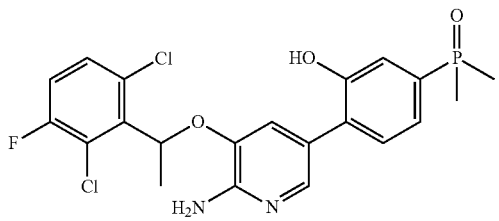 [SMILES: CC(Oc1cc(-c2ccc(P(C)(C)=O)cc2O)cnc1N)c1c(Cl)ccc(F)c1Cl]

A mixture of 3-[1-(2,6-dichloro-3-fluoro-phenyl)ethoxy]-5-(4-dimethylphosphoryl-2-methoxy-phenyl)pyridin-2-amine (30 mg) and pyridine HCl salt (0.5 g) was heated to −205° C. for 30 minutes under N$_2$. The reaction mixture was cooled down to room temperature and purified by reverse phase HPLC (water/methanol, 10-100%) as a gummy solid (4 mg); ESMS: m/z 469 (M+H)$^+$.

Example 18

3-[1-(2,6-dichloro-3-fluoro-phenyl)ethoxy]-5-(5-dimethylphosphoryl-2-pyridyl)pyridin-2-amine

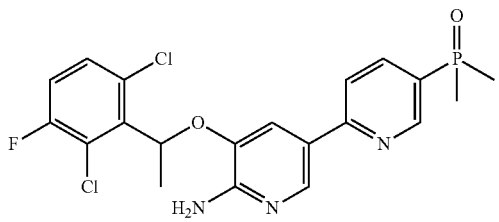 [SMILES: CC(Oc1cc(-c2ccc(P(C)(C)=O)cn2)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 5-bromo-2-pyridinylboronic acid, and dimethylphosphine oxide following the same procedures as Example 1 Step 1 and Step 3; ESMS: m/z 454 (M+H)$^+$.

Example 19

5-(2-chloro-4-dimethylphosphoryl-phenyl)-3-[1-(2,6-dichloro-3-fluoro-phenyl)ethoxy]pyridin-2-amine

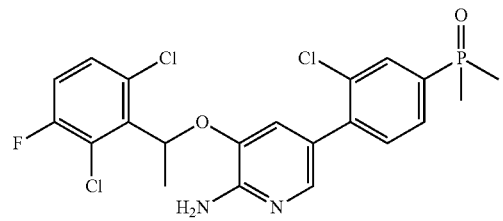

The title compound was prepared from 5-bromo-3-[1-(2,6-dichloro-3-fluoro-phenyl)-ethoxy]-pyridin-2-ylamine, 4-bromo-2-chlorophenyl boronic acid, and dimethylphosphine oxide following the same procedures as Example 1 Step 1 and Step 3; ESMS: m/z 487 (M+H)$^+$.

Example 20

3-[1-(2,6-dichloro-3-fluoro-phenyl)ethoxy]-5-[4-dimethylphosphoryl-2-(trifluoromethoxy)phenyl]pyridin-2-amine

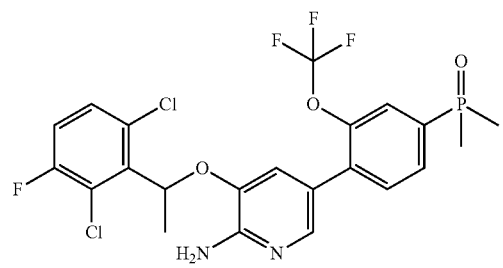 [SMILES: CC(Oc1cc(-c2ccc(P(C)(C)=O)cc2OC(F)(F)F)cnc1N)c1c(Cl)ccc(F)c1Cl]

The title compound was prepared from 5-bromo-3-[1-(2,6-dichloro-3-fluoro-phenyl)-ethoxy]-pyridin-2-ylamine, 4-bromo-2-trifluoromethoxyphenyl boronic acid, and dimethylphosphine oxide following the same procedures as Example 1 Step 1 and Step 3; ESMS: m/z 537 (M+H)$^+$.

Example 21

3-[1-(2,5-dichlorophenyl)ethoxy]-5-(4-dimethylphosphorylphenyl)pyridin-2-amine

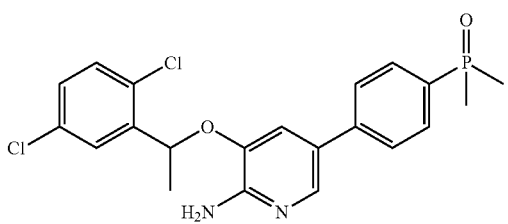 [SMILES: CC(Oc1cc(-c2ccc(P(C)(C)=O)cc2)cnc1N)c1cc(Cl)ccc1Cl]

The title compound was prepared from 5-bromo-3-[1-(2,5-dichloro-phenyl)-ethoxy]-pyridin-2-ylamine, 4-bromophenyl boronic acid, and dimethylphosphine oxide following the same procedures as Example 1 Step 1 and Step 3; ESMS: m/z 435 (M+H)$^+$.

Example 22

3-[1-(2-chloro-5-fluoro-phenyl)ethoxy]-5-(4-dimethylphosphorylphenyl)pyridin-2-amine

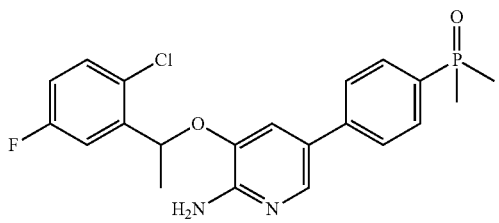 [SMILES: CC(Oc1cc(-c2ccc(P(C)(C)=O)cc2)cnc1N)c1cc(F)ccc1Cl]

The title compound was prepared from 5-bromo-3-[1-(2-chloro5-fluoro-phenyl)-ethoxy]-pyridin-2-ylamine, 4-bromophenylboronic acid, and dimethylphosphine oxide following the same procedures as Example 1 Step 1 and Step 3; ESMS: m/z 418 (M+H)$^+$.

Example 23

3-[(1R)-1-(2,6-dichloro-3-fluoro-phenyl)ethoxy]-5-(4-dimethylphosphorylphenyl)pyridin-2-amine

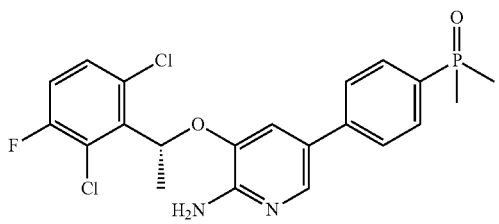

Step 1: Synthesis of 5-bromo-3-hydroxyl-2-nitropyridine

5-Bromo-3-hydroxylpyridine (2 g, 0.011 mol) was dissolved in concentrated sulfuric acid (6 mL), fuming nitric acid (0.52 mL, 0.011 mol) was added under ice-cooling, and the mixture was stirred for 20 hours. The reaction mixture was gently poured into ice water and the mixture was stirred. The precipitated solid was filtered and washed with water to give the object product as a pale-yellow solid (2.2 g, yield 90%).

Step 2: Synthesis of 5-bromo-3-[(1R)-1-(2,6-dichloro-3-fluorophenyl)ethoxy]-2-nitropyridine To a stirred solution of triphenyl phosphine (9.4 g, 0.036 mol) and DIAD (7.2 g. 0.036 mol) in THF (100 mL) at 0° C. was added a solution of (S)-1-(2,6-dichloro-3-fluorophenyl)ethanol (4.55 g, 0.021 mol) and 5-bromo-3-hydroxy-2-nitropyridine (3.35 g, 0.023 mol) in THF (200 mL). The resulting bright orange solution was stirred under a nitrogen atmosphere at ambient temperature for 4 hours at which point all starting materials had been consumed. The solvent was removed, and the crude material was dry loaded onto silica gel, and eluted with ethyl acetate-hexanes (20:80) to yield the title compound as a white solid (8.6 g, 85%).

Step 3: Synthesis of 5-bromo-3-[1-(R)-(2,6-dichloro-3-fluoro-phenyl)-ethoxy]-pyridin-2-ylamine To a stirred mixture of AcOH (150 mL) and EtOH (150 mL) was suspended 5-bromo-3-[(1R)-1-(2,6-dichloro-3-fluorophenyl)ethoxy]-2-nitropyridine (6.6 g, 0.016 mol) and iron chips (8.8 g, 0.16 mol). The reaction was heated slowly to reflux and allowed to stir for 1 hour. The reaction was cooled to room temperature then diethyl ether (100 mL) and water (100 mL) was added. The solution was carefully neutralized by the addition of sodium carbonate. The combined organic extracts were washed with saturated NaHCO$_3$ (2×100 mL), H$_2$O (2×100 mL) and brine (1×100 mL) then dried over Na$_2$SO$_4$, filtered and concentrated to dryness under vacuum to yield the title compound as a white solid (5.0 g, 84%).

Step 4: The title compound was prepared from 5-bromo-3-[(1R)-1-(2,6-dichloro-3-fluoro-phenyl)-ethoxy]-pyridin-2-ylamine, 4-bromophenyl boronic acid, and dimethylphosphine oxide following the same procedures as Example 1 Step 1 and Step 3; ESMS: m/z 453 (M+H)$^+$; chiral purity 99.87% (column AD-H 4.6*250 mm 5 um; solvent:hexane/isopropanol).

Example 24

3-[(1R)-1-(2,6-dichloro-3-fluoro-phenyl)ethoxy]-5-(4-dimethylphosphoryl-2-methoxy-phenyl)pyridin-2-amine

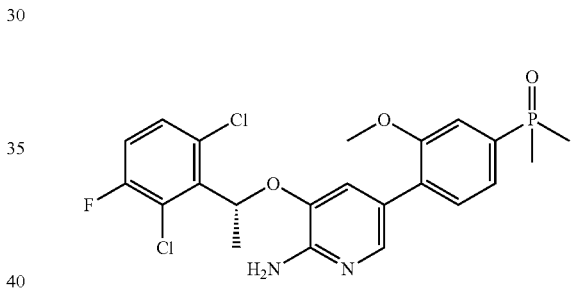

The title compound was prepared from 5-bromo-3-[(1R)-1-(2,6-dichloro-3-fluoro-phenyl)-ethoxy]-pyridin-2-ylamine, 4-bromo2-methoxy-phenyl boronic acid, and dimethylphosphine oxide following the same procedures as Example 1 Step 1 and Step 3; ESMS: m/z 483 (M+H)$^+$; chiral purity 99.82% (column AD-H 4.6*250 mm 5 um; solvent: hexane/isopropanol).

Example 25

3-[(1R)-1-(2,6-dichloro-3-fluoro-phenyl)ethoxy]-5-(4-dimethylphosphoryl-2-fluoro-phenyl)pyridin-2-amine

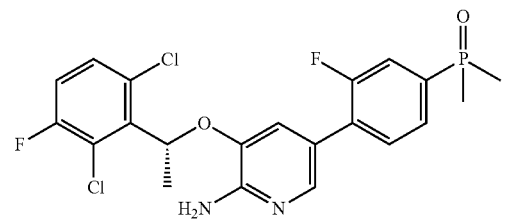 [SMILES: C[C@@H](Oc1cc(-c2ccc(P(C)(C)=O)cc2F)cnc1N)c1c(Cl)ccc(F)c1Cl]

The title compound was prepared from 5-bromo-3-[(1R)-1-(2,6-dichloro-3-fluoro-phenyl)-ethoxy]-pyridin-2-ylamine, 4-bromo-2-fluoro-phenylboronic acid, and dimethylphosphine oxide followed the same procedures as Example 1 Step 1 and Step 3; ESMS: m/z 471 (M+H)⁺; chiral purity 93.12% (column AD-H 4.6*250 mm 5 um; solvent:hexane/isopropanol).

Example 26

3-[1-2-(2-chloro-5-fluoro-phenyl)ethoxy]-5-(4-diethoxyphosphorylphenyl)pyridine-2-amine

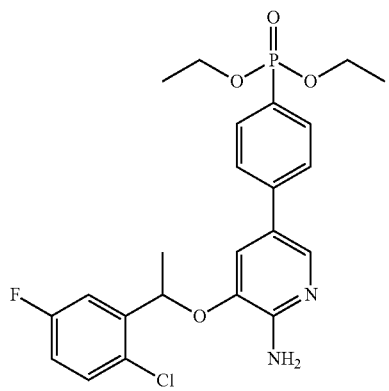 [SMILES: CCOP(=O)(OCC)c1ccc(-c2cnc(N)c(OC(C)c3cc(F)ccc3Cl)c2)cc1]

The title compound was prepared from 5-bromo-3-[1-(2-chloro-5-fluoro-phenyl)-ethoxy]-pyridin-2-ylamine, 4-bromo-phenyl boronic acid, and diethyl phosphite following the same procedures as Example 1 Step 1 and Step 3; ESMS: m/z 479 (M+H)⁺.

Example 27

[4-(6-amino-5-[1-(2-chloro-5-fluoro-phenyl)ethoxyl]-3-pyridyl]phenyl]phosphonic acid

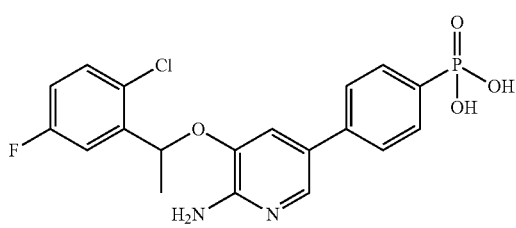 [SMILES: CC(Oc1cc(-c2ccc(P(=O)(O)O)cc2)cnc1N)c1cc(F)ccc1Cl]

A solution of 3-[1-2-(2-chloro-5-fluoro-phenyl)ethoxy]-5-(4-diethoxyphosphorylphenyl)pyridine-2-amine (0.045 g, 0.094 mmol), bromotrimethylsilane (0.4 mL, 4.70 mmol), and CH₂Cl₂ (10 mL) was stirred for 30 minutes and then HMDS (1 mL, 47.96 mmol) was added. The resulting mixture was stirred overnight and then concentrated in vacuo. Approximately 5 mL of MeOH was added and subsequently removed in vacuo. This procedure was repeated 2 times. The crude material was purified with preparative HPLC (water/methanol, 10-100%) using methanol and aqueous TFA buffer to afford the title compound as a white powder (15 mg); ESMS: m/z 422 (M+H)⁺.

Example 28

3-[(1R)-1-2-(2,6-dichloro-3-fluoro-phenyl)ethoxy]-5-(4-diethoxyphosphorylphenyl)pyridine-2-amine

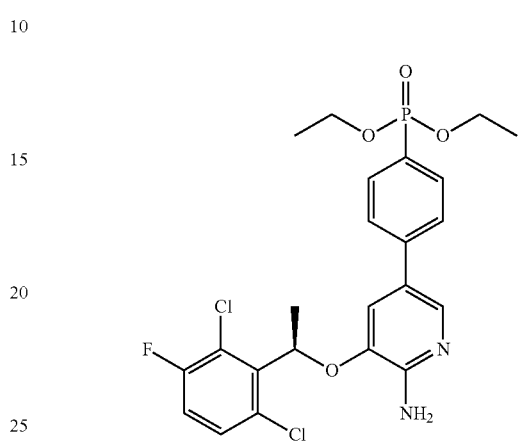

The title compound was prepared from 5-bromo-3-[1(R)-1-(2,6-dichloro-3-fluoro-phenyl)-ethoxy]-pyridin-2-ylamine, 4-bromo-phenyl boronic acid, and diethyl phosphite following the same procedures as Example 1 Step 1 and Step 3; ESMS: m/z 513 (M+H)⁺.

Example 29

[4-(6-amino-5-[(1R)-1-(2,6-dichloro-3-fluoro-phenyl)ethoxyl]-3-pyridyl]phenyl]phosphonic acid

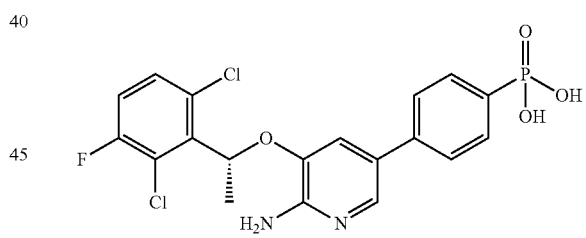

The title compound was prepared from 3-[(1R)-1-2-(2,6-dichloro-3-fluoro-phenyl)ethoxy]-5-(4-diethoxyphosphorylphenyl)pyridine-2-amine following the same procedures as Example 27; ESMS: m/z 457 (M+H)⁺.

What is claimed is:
1. A compound of formula (I), or a pharmaceutically acceptable salt, solvate or hydrate thereof,

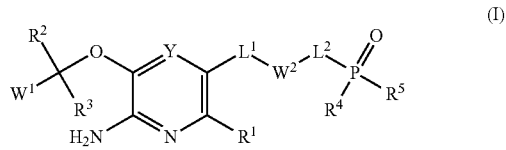

(I)

wherein Y is N, or CR⁶;

$L^1$ and $L^2$ are independently selected from the group consisting of a bond, —O—, —N(H)—, —S—, —OR$^6$—, —SR$^6$—, —NR$^6$—, —R$^6$NR$^7$—, —R$^6$OR$^7$—C(O)N(R$^6$)—, —NR$^6$C(O)—, —C(O)NR$^6$—, —R$^6$S(O)$_2$—, —R$^6$S(O)$_r$R$^7$—, —R$^6$S(O)$_2$NR$^7$—, —NR$^6$S(O)$_2$R$^7$—, —C(O)R$^6$—, —OC(O)NR$^6$—, unsubstituted or substituted alkyl, unsubstituted or substituted alkenyl, unsubstituted or substituted alkynyl, unsubstituted or substituted $C_{6-12}$ aryl, unsubstituted or substituted $C_{3-12}$ carbocyclic, unsubstituted or substituted 3- to 12-membered heterocyclyl, and unsubstituted or substituted 3- to 12-membered heteroaryl; where $L^1$ and $L^2$ can be attached to in any position of the group; and where r is an integer from 0-2;

$W^1$ is selected from the group consisting of unsubstituted or substituted $C_{3-12}$ carbocyclic, unsubstituted or substituted 3- to 12-membered heterocyclyl, unsubstituted or substituted $C_{6-12}$ aryl, unsubstituted or substituted heteroaryl, when $C_{6-12}$ aryl or heteroaryl is substituted with only two substituents, the two substituents are not in para positions;

$W^2$ is selected from the group consisting of unsubstituted or substituted $C_{6-12}$ aryl, and unsubstituted or substituted 3- to 12-membered heteroaryl;

$R^1$ is selected from the group consisting of hydrogen, halogen, unsubstituted or substituted alkyl, unsubstituted or substituted alkenyl, unsubstituted or substituted alkynyl, —SR$^6$, —S(O)R$^6$, —S(O)$_2$R$^6$, —S(O)$_2$NR$^6$R$^7$, —NO$_2$, —NR$^6$R$^7$, —CN, —C(O)R$^6$, —OC(O)R$^6$, —OR$^6$, —CONR$^6$R$^7$, —NR$^6$C(O)R$^7$, unsubstituted or substituted $C_{3-12}$ cycloalkyl, unsubstituted or substituted $C_{6-12}$ aryl, unsubstituted or substituted 3- to 12-membered heterocyclic, and unsubstituted or substituted 5- to 12-membered heteroaryl;

$R^2$ and $R^3$ are independently selected from the group consisting of hydrogen, halogen, unsubstituted or substituted alkyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl; and $R^4$ and $R^5$ are independently selected from the group consisting —OR$^6$, —NR$^6$R$^7$, unsubstituted or substituted alkyl, unsubstituted or substituted alkenyl, unsubstituted or substituted alkynyl, and unsubstituted or substituted $C_3$-$C_{10}$ cycloalkyl; or $R^4$ and $R^5$ together with atom(s) to which they are attached form an unsubstituted or substituted 3- to 12-membered ring;

wherein $R^6$ and $R^7$ are independently selected from the group consisting of hydrogen, halogen, unsubstituted or substituted $C_{1-12}$ alkyl, unsubstituted or substituted $C_{2-12}$ alkenyl, unsubstituted or substituted $C_{2-12}$ alkynyl, unsubstituted or substituted $C_{3-12}$ cycloalkyl, unsubstituted or substituted $C_{6-12}$ aryl, unsubstituted or substituted 3-12 membered heterocyclic, and unsubstituted or substituted 5-12 membered heteroaryl.

2. The compound of claim 1, or a pharmaceutically acceptable salt, solvate or hydrate thereof, wherein $W^1$ is substituted $C_{6-12}$ aryl, or substituted heteroaryl, and wherein $W^1$ has 1 to 4 substituents independently selected from the group consisting of halogen, —CN, —NO$_2$, —OR$^6$, —SR$^6$, —N(R$^6$)R$^7$, —C(O)NR$^6$R$^7$, —NR$^6$C(O)R$^7$, —S(O)$_2$R$^6$, —R$^6$SO$_2$NR$^7$, —C(O)R$^6$, —OC(O)NR$^6$R$^7$, unsubstituted or substituted alkyl, unsubstituted or substituted alkenyl, and unsubstituted or substituted alkynyl.

3. The compound of claim 1, or a pharmaceutically acceptable salt, solvate or hydrate thereof, wherein $W^1$ has three substituents.

4. The compound of claim 1, or a pharmaceutically acceptable salt, solvate or hydrate thereof, wherein $W^1$ is phenyl substituted with at least two halogens.

5. The compound of claim 1, or a pharmaceutically acceptable salt, solvate or hydrate thereof, wherein $W^1$ is 2,6-dichloro-3-fluoro-phenyl.

6. The compound of claim 1, or a pharmaceutically acceptable salt, solvate or hydrate thereof, wherein $W^2$ is substituted $C_{6-12}$ aryl or substituted heteroaryl, where $W^2$ has 1 to 4 substituents independently selected from the group consisting of halogen, —CN, —NO$_2$, —OR$^6$, —SR$^6$, —N(R$^6$)R$^7$, —C(O)NR$^6$R$^7$, —NR$^6$C(O)R$^7$, —S(O)$_2$R$^6$, —C(O)R$^6$, —OC(O)NR$^6$R$^7$, unsubstituted or substituted alkyl, unsubstituted or substituted alkenyl, and unsubstituted or substituted alkynyl.

7. The compound of claim 6, or a pharmaceutically acceptable salt, solvate or hydrate thereof, wherein $W^2$ is substituted $C_{6-12}$ aryl or substituted heteroaryl, and wherein $W^2$ has 1 to 4 substituents independently selected from the group consisting of halogen, and —OR$^6$.

8. The compound of claim 1, or a pharmaceutically acceptable salt, solvate or hydrate thereof, wherein $W^2$ is selected from the group consisting of unsubstituted or substituted phenyl, unsubstituted or substituted pyridyl, unsubstituted or substituted pyrazol, unsubstituted or substituted imidazol, unsubstituted or substituted pyrrol, tetrazol, unsubstituted or substituted oxazol, unsubstituted or substituted oxadiazol, unsubstituted or substituted thiazol, unsubstituted or substituted pyrimidyl, and unsubstituted or substituted naphthalenyl.

9. The compound of claim 8, or a pharmaceutically acceptable salt, solvate or hydrate thereof, wherein $W^2$ is selected from the group consisting of unsubstituted or substituted phenyl.

10. The compound of claim 9, or a pharmaceutically acceptable salt, solvate or hydrate thereof, wherein $W^2$ is selected from the group consisting of phenyl, 2-methoxy-phenyl, and 2-fluoro-phenyl.

11. The compound of claim 1, or a pharmaceutically acceptable salt, solvate or hydrate thereof, wherein $L^1$ and $L^2$ are a bond.

12. The compound of claim 1, or a pharmaceutically acceptable salt, solvate or hydrate thereof, wherein Y is CR$^6$.

13. The compound of claim 12, or a pharmaceutically acceptable salt, solvate or hydrate thereof, wherein $R^6$ is hydrogen.

14. The compound of claim 1, or a pharmaceutically acceptable salt, solvate or hydrate thereof, wherein $R^1$ is selected from the group consisting of hydrogen, halogen, unsubstituted or substituted alkyl, —SR$^6$, —S(O)R$^6$, —S(O)$_2$R$^6$, —S(O)$_2$NR$^6$R$^7$, —NO$_2$, —NR$^6$R$^7$, —CN, —C(O)R$^6$, —OC(O)R$^6$, —OR$^6$, —CONR$^6$R$^7$, and —NR$^6$C(O)R$^7$.

15. The compound of claim 14, or a pharmaceutically acceptable salt, solvate or hydrate thereof, wherein $R^1$ is hydrogen.

16. The compound of claim 1, or a pharmaceutically acceptable salt, solvate or hydrate thereof, wherein $R^2$ and $R^3$ are independently selected from the group consisting of hydrogen, and unsubstituted or substituted alkyl.

17. The compound of claim 16, or a pharmaceutically acceptable salt, solvate or hydrate thereof, wherein at least one of $R^2$ and $R^3$ is hydrogen.

18. The compound of claim 17, or a pharmaceutically acceptable salt, solvate or hydrate thereof, wherein at least one of $R^2$ and $R^3$ is unsubstituted or substituted $C_{1-6}$ alkyl.

19. The compound of claim 18, or a pharmaceutically acceptable salt, solvate or hydrate thereof, wherein at least one of $R^2$ and $R^3$ is methyl.

20. The compound of claim 1, or a pharmaceutically acceptable salt, solvate or hydrate thereof, wherein $R^2$ is hydrogen, and $R^3$ is methyl.

21. The compound of claim 1, or a pharmaceutically acceptable salt, solvate or hydrate thereof, wherein the compound has more R-form than S-form.

22. The compound of claim 1, or a pharmaceutically acceptable salt, solvate or hydrate thereof, wherein $R^4$ and $R^5$ are independently selected from the group consisting of unsubstituted or substituted alkyl, and —$OR^6$; and wherein $R^6$ is selected from the group consisting of hydrogen, and unsubstituted or substituted alkyl.

23. The compound of claim 22, or a pharmaceutically acceptable salt, solvate or hydrate thereof, wherein $R^4$ and $R^5$ are methyl.

24. The compound of claim 22, or a pharmaceutically acceptable salt, solvate or hydrate thereof, wherein at least one of $R^4$ and $R^5$ is —$OR^6$, and $R^6$ is hydrogen.

25. A compound of formula (Ic), or a pharmaceutically acceptable salt, solvate or hydrate thereof,

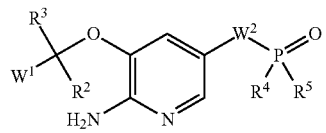

(Ic)

where $W^1$ is $C_{6-12}$ aryl substituted with three substituents;
  $W^2$ is selected from the group consisting of unsubstituted or substituted $C_{6-12}$ aryl, and unsubstituted or substituted 3- to 12-membered heteroaryl;
  $R^2$ and $R^3$ are independently selected from the group consisting of hydrogen, and unsubstituted or substituted alkyl; and
  $R^4$ and $R^5$ are independently selected from the group consisting —$OR^6$, and unsubstituted or substituted alkyl, wherein $R^6$ is selected from the group consisting of hydrogen, halogen, and unsubstituted or substituted $C_{1-12}$ alkyl.

26. The compound of claim 25, wherein $W^1$ is phenyl substituted with three halogens.

27. The compound of claim 25, wherein $R^4$ and $R^5$ are methyl.

28. A compound has a formula selected from the group consisting of:

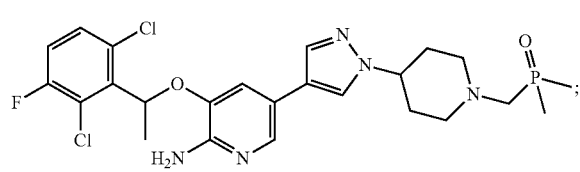

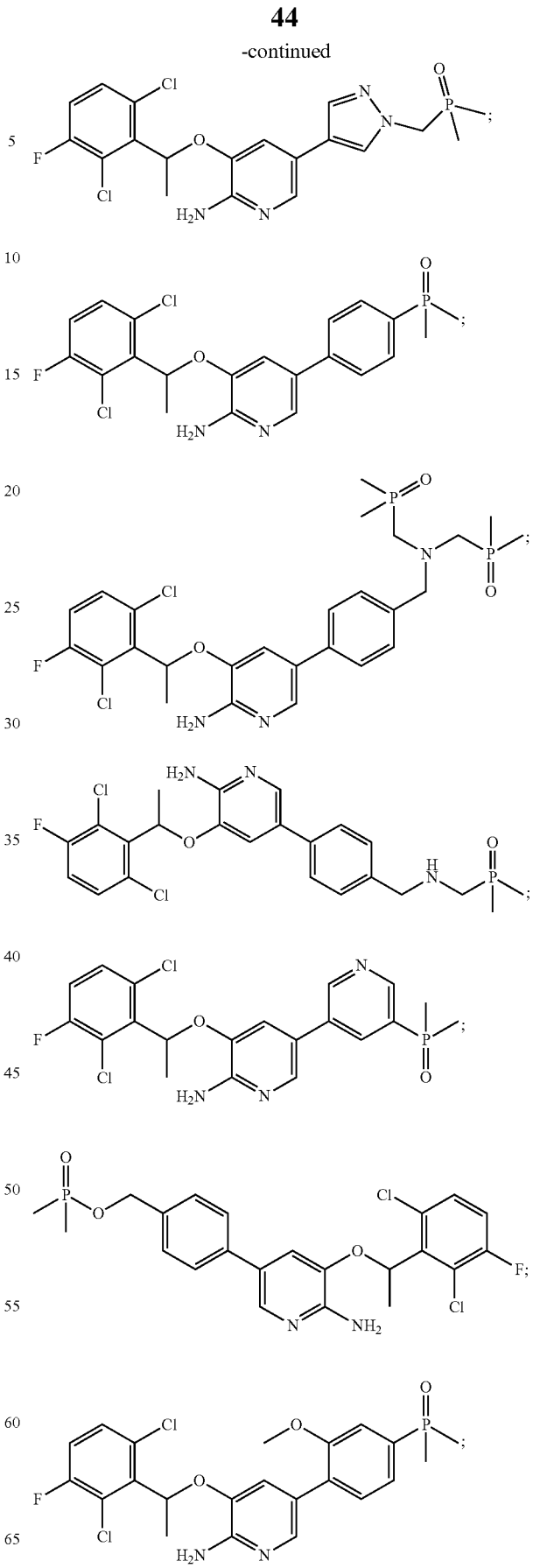

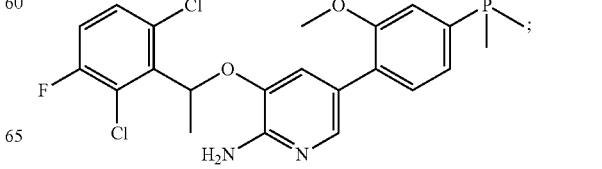

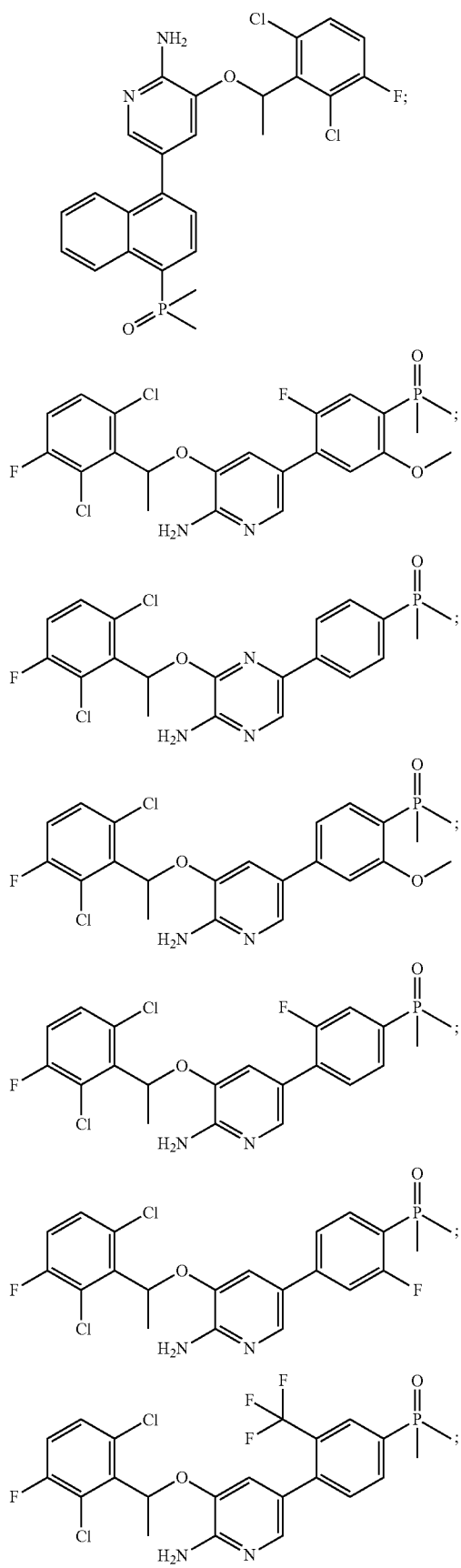
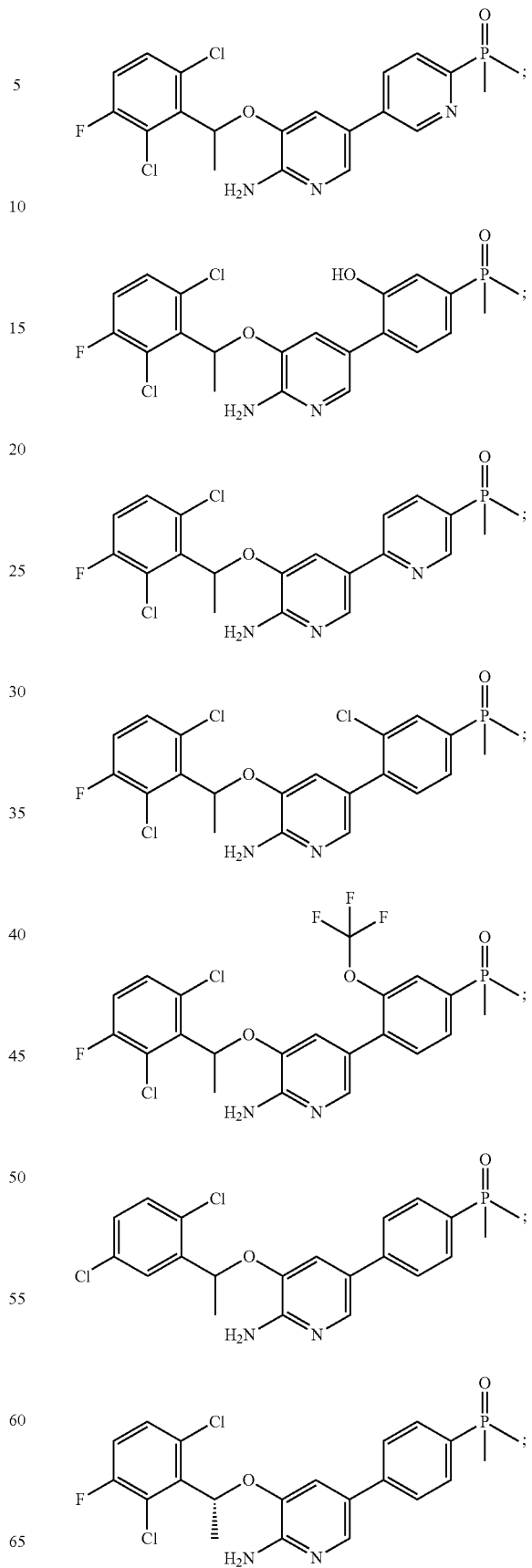

30. A pharmaceutical composition comprising the compound of claim 1, and a pharmaceutically acceptable carrier.

31. The compound of claim 28, which has a formula of:

32. The compound of claim 28, which has a formula of:

33. The compound of claim 28, which has a formula of:

29. A compound has a formula selected from the group consisting of:

* * * * *